US005683872A

United States Patent [19]
Rudert et al.

[11] Patent Number: 5,683,872
[45] Date of Patent: Nov. 4, 1997

[54] POLYMERS OF OLIGONUCLEOTIDE PROBES AS THE BOUND LIGANDS FOR USE IN REVERSE DOT BLOTS

[75] Inventors: William A. Rudert, Sarver; Massimo Trucco, Pittsburgh, both of Pa.

[73] Assignee: University of Pittsburgh, Pittsburgh, Pa.

[21] Appl. No.: 363,585

[22] Filed: Dec. 23, 1994

Related U.S. Application Data

[63] Continuation of Ser. No. 786,228, Oct. 31, 1991, abandoned.

[51] Int. Cl.$^6$ .............................. C12Q 1/68; C12P 19/34
[52] U.S. Cl. ................................. 435/6; 435/91.2
[58] Field of Search .................. 435/6, 91.2; 935/77, 935/78

[56] References Cited

U.S. PATENT DOCUMENTS

| | | | |
|---|---|---|---|
| 5,124,246 | 6/1992 | Urden et al. | 435/6 |
| 5,212,059 | 5/1993 | Schwartz et al. | 435/6 |

FOREIGN PATENT DOCUMENTS

| | | | |
|---|---|---|---|
| 9108307 | 6/1991 | WIPO . | |

OTHER PUBLICATIONS

Saiki et al PNAS 86: 6230–6234 (1989).

Mullis, Cold Spring Harbor Symp. 263–273 (1986) "Specific enzymatic amplification . . . " USB Catalogue (1990) p. 152.

Roewer et al. Electrophoresis: 12(2–3):181–186 (1991) "Hybridization and PCR . . . ".

Saiki et al. PNAS 86:6230–6234 (1989) "Genetic analysis of amplified DNA . . . ".

Murray et al., Mol. Biochem. Porasit. 30:209–216 (1988) "Cloning and characterization of a species . . . ".

Matthews et al., Analyt. Biochem 169:1–25 (1988) "Analytical strategies for the use of DNA probes".

*Primary Examiner*—Eggerton A. Campbell
*Attorney, Agent, or Firm*—Reed Smith Shaw & McClay

[57] ABSTRACT

A method of detecting nucleic acid sequences in which polymers of selected oligonucleotide probes which are complementary to a region in a nucleic acid sequence that is to be detected are bound to a substrate. The polymers bound to the substrate contain multiple randomly repeated copies of a specific oligonucleotide probe and may be synthesized using enzymatic amplification techniques.

23 Claims, 14 Drawing Sheets

1

4

6

7

Polymers:

| | |
|---|---|
| DRB1001 TAAGTTTGAATGTCATTT | DRB2801 CGGTTGCTGGAAAGATGC |
| DRB1002 CCTAAGAGGAGTGTCAT | DRB2802 GGTTACTGGAGAGACACT |
| DRB1003 GTACTCTACGTCTGAGTG | DRB2803 TGGAAAGACTCTTCTATA |
| DRB1004 GAGCAGGTTAAACATGAG | DRB2804 GTATCTGCACAGAGCAT |
| DRB1005 AGAAATAACACTCACCCG | DRB2805 GTTCCTGCACAGAGACAT |
| DRB1006 TGGCAGGGTAAGTATAAG | DRB2806 GTTCCTGCACAGAGGCAT |
| DRB1007 GAAGCAGGATAAGTTTGA | DRB2807 GCGGTACCTGGACAGATA |
| DRB1008 GAGGAGGTTAAGTTTGAG | DRB2808 GTTCCTGGAGAGACACTT |
| DRB1009 CAGCAGGATAAGTATGAG | DRB2809 TTCCTGGAGAGATACTTC |
| DRB1010 GAGCTGCGTAAGTCTGAG | DRB2810 GCGAGTGTGGAACCTGAT |
| DRB1011 GAGCTGCTTAAGTCTGAG | DRB2811 GCGAGTCTGGAACCTGAT |
| DRB1012 GAGCAGGCTAAGTGTGAG | DRB2812 AAGTATCTCCCAGAGAAC |
| DRB1013 TCTGAGTGTCAATTCTTC | DRB2813 GTTCCTGGACAGATACTT |

| | |
|---|---|
| DRB8601 AACTACGGGGTTGGTGAG | |
| DRB8602 AACTACGGGGCTGTGGAG | |
| DRB8603 AACTACGGGGTTGTGGAG | |

| | |
|---|---|
| DRB3701 CCAAGAGGAGTCCGTGCG | |
| DRB3702 AACCAGGAGGAGTCCGTG | |
| DRB3703 ACCAGGAGGAGAACGTGC | |
| DRB3704 ATCACCAAGAGGAGTACG | |
| DRB3705 CCAGGAGGAGCTCCTGCG | |
| DRB3706 CCAAGAGGAATACGTGCG | |
| DRB3707 AACCAAGAGGAGAACGTG | |
| DRB3708 GCGGTACTCCTCCTTGGT | |
| DRB3709 GGAGACTTGCGCTTCGA | |
| DRB3710 CAGGAGAGTTCCTGCGC | |
| DRB3711 AGGAGGAGTACGCGCGCT | |
| DRB3712 CAGGAGGAGTTCGTGCGC | |
| DRB3713 GCGCACGTACTCCTCTTG | |
| DRB3714 TAACCAAGAGGAGTCCGT | |
| DRB3715 ATCACCAAGAGGAGTCCG | |
| DRB3716 AACGGGAGGAGAACCTGC | |

| | |
|---|---|
| DBB5701 GCCTGATGCCGAGTACTG | DRB7001 TCCTGGAGCAGAGAGGCGGG |
| DRB5702 GCCTAGCGCCGAGTACTG | DRB7002 GACTTCCTGGAAGACAGG |
| DRB5703 GCCTGATGAGGAGTACTG | DRB7003 GACCTCCTGGAAGACAGG |
| DRB5701 GCCTGCTGCGGAGCACTG | DRB7004 GGCCGGGTGGACAACTAC |
| DRB5705 GCCTGTCGCCGAGTACTG | DRB7005 ACCGGCGCCCGCTTCTGC |
| DRB5706 GCCTGACGCTGAGTACTG | DRB7006 GCAGAGGCGGGCCGGAGT |
| DRB5707 GCCTGACGCCGAGTACTG | DRB7007 ACATCCTGGAAGACGAGC |
| DRB5708 GCCTGATGCTGAGTACTG | DRB7008 ACTTCCTGGAAGACGAGC |
| DRB5709 GCCTGTTGCCGAGTCCTG | DRB7009 AGCGGAGGCGGGCCGAGG |
| | DRB7010 GGACATCCTGGAAGACAG |
| | DRB7011 GACATCCTGGAGCAGGCG |
| | DRB7012 ACCTGGCCCGCCTCTGC |

FIG. 11A

Primers:

DR1 = A: TTCTTGTGGCAGCTTAAGTT
      B: CCGCTGCACTGTGAAGCTCT

DR2 = A: TTCCTGTGGCAGCCTAAGAGG
      B: CCGCTGCACTGTGAAGCTCT

DR4 = A: GTTTCTTGGAGCAGGTTAAAC
      B: CCGCTGCACTGTGAAGCTCT

DRw52 associated =   A: CACGTTTCTTGGAGTACTCTAC
                     B: CCGCTGCACTGTGAAGCTCT DRw52 - DRB3 =   A: CCCAGCACGTTTCTTGGAGCT
                 B: CCGCTGCACTGTGAAGCTCT

SEQUENCE LISTING ( 1 ) GENERAL INFORMATION:

( i i i ) NUMBER OF SEQUENCES: 112

( 2 ) INFORMATION FOR SEQ ID NO:1:

( i ) SEQUENCE CHARACTERISTICS:
        ( A ) LENGTH: 17 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x i ) SEQUENCE DESCRIPTION: SEQ ID NO: 1:

CTTCGACAGC GACGTGG    17

( 2 ) INFORMATION FOR SEQ ID NO:2:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( x ) PUBLICATION INFORMATION:
        ( A ) AUTHORS: Rudert, William A.
            Trucco, Massimo
        ( B ) TITLE: DNA Polymers of Protein Binding Sequences
            Generated by PCR
        ( C ) JOURNAL: Nucleic Acids Research
        ( D ) VOLUME: 18
        ( F ) PAGES: 6460
        ( G ) DATE: 1990
        ( K ) RELEVANT RESIDUES IN SEQ ID NO: 2: 1 to 18

( x i ) SEQUENCE DESCRIPTION: SEQ ID NO: 2:

AAAAAATGTC TGCCTAGA    18

( 2 ) INFORMATION FOR SEQ ID NO:3:

( i ) SEQUENCE CHARACTERISTICS:
        ( A ) LENGTH: 31 nucleotides
        ( B ) TYPE: nucleic acid
        ( C ) STRANDEDNESS: single
        ( D ) TOPOLOGY: linear ( i i ) MOLECULE TYPE: synthetic DNA ( x ) PUBLICATION INFORMATION:
        ( A ) AUTHORS: Rudert, William A.
            Trucco, Massimo (B) TITLE: DNA Polymers of Protein Binding Sequences
  Generated by PCR
(C) JOURNAL: Nucleic Acids Research
(D) VOLUME: 18
(F) PAGES: 6460
(G) DATE: 1990
(K) RELEVANT RESIDUES IN SEQ ID NO: 3: 1 to 31

(xi) SEQUENCE DESCRIPTION: SEQ ID NO: 3:

CTAGATATCA AAAAATGTCT GCCTAGATAT C          31

(2) INFORMATION FOR SEQ ID NO:4:

(i) SEQUENCE CHARACTERISTICS:
      (A) LENGTH: 28 nucleotides
      (B) TYPE: nucleic acid
      (C) STRANDEDNESS: single
      (D) TOPOLOGY: linear (ii) MOLECULE TYPE: synthetic DNA (x) PUBLICATION INFORMATION:
      (A) AUTHORS: Rudert, William A.
         Trucco, Massimo
      (B) TITLE: DNA Polymers of Protein Binding Sequences
         Generated by PCR
      (C) JOURNAL: Nucleic Acids Research
      (D) VOLUME: 18
      (F) PAGES: 6460
      (G) DATE: 1990
      (K) RELEVANT RESIDUES IN SEQ ID NO: 4: 1 to 28

(xi) SEQUENCE DESCRIPTION: SEQ ID NO: 4:

GCAGACATTT TTTGATATCT AGGCAGAC             28

(2) INFORMATION FOR SEQ ID NO:5:

(i) SEQUENCE CHARACTERISTICS:
      (A) LENGTH: 44 nucleotides
      (B) TYPE: nucleic acid
      (C) STRANDEDNESS: single
      (D) TOPOLOGY: linear (ii) MOLECULE TYPE: synthetic DNA (x) PUBLICATION INFORMATION:
      (A) AUTHORS: Rudert, William A.
         Trucco, Massimo
      (B) TITLE: DNA Polymers of Protein Binding Sequences
         Generated by PCR
      (C) JOURNAL: Nucleic Acids Research
      (D) VOLUME: 18
      (F) PAGES: 6460
      (G) DATE: 1990
      (K) RELEVANT RESIDUES IN SEQ ID NO: 5: 1 to 44

(xi) SEQUENCE DESCRIPTION: SEQ ID NO: 5:

CTAGATATCA AAAAATGTCT GCCTAGATAT CAAAAAATGT CTGC    44

(2) INFORMATION FOR SEQ ID NO:6:

(i) SEQUENCE CHARACTERISTICS:
      (A) LENGTH: 44 nucleotides
      (B) TYPE: nucleic acid
      (C) STRANDEDNESS: single
      (D) TOPOLOGY: linear (ii) MOLECULE TYPE: synthetic DNA (x) PUBLICATION INFORMATION:
      (A) AUTHORS: Rudert, William A.
         Trucco, Massimo
      (B) TITLE: DNA Polymers of Protein Binding Sequences
         Generated by PCR ( C ) JOURNAL: Nucleic Acids Research
        ( D ) VOLUME: 18
        ( F ) PAGES: 6460
        ( G ) DATE: 1990
        ( K ) RELEVANT RESIDUES IN SEQ ID NO: 6: 1 to 44

( x i ) SEQUENCE DESCRIPTION: SEQ ID NO: 6:

GCAGACATTT TTTGATATCT AGGCAGACAT TTTTGATAT CTAG                44

( 2 ) INFORMATION FOR SEQ ID NO:7:

( i ) SEQUENCE CHARACTERISTICS:
        ( A ) LENGTH: 66 nucleotides
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO: 7:

CTAGATATCA AAAAATGTCT GCCTAGATAT CAAAAAATGT CTGCCTAGAT ATCAAAAAAT    60

GTCTGC    66

( 2 ) INFORMATION FOR SEQ ID NO:8:

( i ) SEQUENCE CHARACTERISTICS:
        ( A ) LENGTH: 66 nucleotides
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO: 8:

GCAGACATTT TTTGATATCT AGGCAGACAT TTTTGATAT CTAGGCAGAC ATTTTTGAT    60

ATCTAG    66

( 2 ) INFORMATION FOR SEQ ID NO:9:

( i ) SEQUENCE CHARACTERISTICS:
        ( A ) LENGTH: 27 nucleotides
        ( B ) TYPE: nucleic acid
        ( C ) STRANDEDNESS: single
        ( D ) TOPOLOGY: linear ( i i ) MOLECULE TYPE: synthetic DNA ( x ) PUBLICATION INFORMATION:
        ( A ) AUTHORS: Rudert, W.A.
                       Trucco, M.
        ( B ) TITLE: A Novel Approach to Rapid HLA Class II
                     Molecular Typing
        ( C ) JOURNAL: HLA 1991
        ( D ) VOLUME: 2
        ( F ) PAGES: 352-356
        ( G ) DATE: 1992
        ( K ) RELEVANT RESIDUES IN SEQ ID NO: 9: 1 to 27

( x i ) SEQUENCE DESCRIPTION: SEQ ID NO: 9:

GCCGAGATCT GGCGGCCTGT TGCCGAG    27

( 2 ) INFORMATION FOR SEQ ID NO:10:

( i ) SEQUENCE CHARACTERISTICS:
        ( A ) LENGTH: 27 nucleotides
        ( B ) TYPE: nucleic acid
        ( C ) STRANDEDNESS: single
        ( D ) TOPOLOGY: linear ( i i ) MOLECULE TYPE: synthetic DNA ( x ) PUBLICATION INFORMATION:
   ( A ) AUTHORS: Rudert, W.A.
         Trucco, M.
   ( B ) TITLE: A Novel Approach to Rapid HLA Class II
         Molecular Typing
   ( C ) JOURNAL: HLA 1991
   ( D ) VOLUME: 2
   ( F ) PAGES: 352-356
   ( G ) DATE: 1992
   ( K ) RELEVANT RESIDUES IN SEQ ID NO: 10: 1 to 27

( x i ) SEQUENCE DESCRIPTION: SEQ ID NO: 10:

GCCGAGATCT GGCGGCCTAG CGCCGAG 27

( 2 ) INFORMATION FOR SEQ ID NO:11:

( i ) SEQUENCE CHARACTERISTICS:
      ( A ) LENGTH: 27 nucleotides
      ( B ) TYPE: nucleic acid
      ( C ) STRANDEDNESS: single
      ( D ) TOPOLOGY: linear ( i i ) MOLECULE TYPE: synthetic DNA ( x ) PUBLICATION INFORMATION:
      ( A ) AUTHORS: Rudert, W.A.
            Trucco, M.
      ( B ) TITLE: A Novel Approach to Rapid HLA Class II
            Molecular Typing
      ( C ) JOURNAL: HLA 1991
      ( D ) VOLUME: 2
      ( F ) PAGES: 352-356
      ( G ) DATE: 1992
      ( K ) RELEVANT RESIDUES IN SEQ ID NO: 11: 1 to 27

( x i ) SEQUENCE DESCRIPTION: SEQ ID NO: 11:

GCCGAGATCT GGCGGCCTGA CGCCGAG 27

( 2 ) INFORMATION FOR SEQ ID NO:12:

( i ) SEQUENCE CHARACTERISTICS:
      ( A ) LENGTH: 27 nucleotides
      ( B ) TYPE: nucleic acid
      ( C ) STRANDEDNESS: single
      ( D ) TOPOLOGY: linear ( i i ) MOLECULE TYPE: synthetic DNA ( x ) PUBLICATION INFORMATION:
      ( A ) AUTHORS: Rudert, W.A.
            Trucco, M.
      ( B ) TITLE: A Novel Approach to Rapid HLA Class II
            Molecular Typing
      ( C ) JOURNAL: HLA 1991
      ( D ) VOLUME: 2
      ( F ) PAGES: 352-356
      ( G ) DATE: 1992
      ( K ) RELEVANT RESIDUES IN SEQ ID NO: 12: 1 to 27

( x i ) SEQUENCE DESCRIPTION: SEQ ID NO: 12:

GCCGAGATCT GGCGGCCTGA TGCCGAG 27

( 2 ) INFORMATION FOR SEQ ID NO:13:

( i ) SEQUENCE CHARACTERISTICS:
      ( A ) LENGTH: 27 nucleotides
      ( B ) TYPE: nucleic acid
      ( C ) STRANDEDNESS: single
      ( D ) TOPOLOGY: linear ( i i ) MOLECULE TYPE: synthetic DNA ( x ) PUBLICATION INFORMATION:

( A ) AUTHORS: Rudert, W.A.
                                   Trucco, M.
                    ( B ) TITLE: A Novel Approach to Rapid HLA Class II
                                 Molecular Typing
                    ( C ) JOURNAL: HLA 1991
                    ( D ) VOLUME: 2
                    ( F ) PAGES: 352-356
                    ( G ) DATE: 1992
                    ( K ) RELEVANT RESIDUES IN SEQ ID NO: 13: 1 to 27

( x i ) SEQUENCE DESCRIPTION: SEQ ID NO: 13:

GCCGAGATCT GGCTGCCTGC CGCCGAG                                    27

( 2 ) INFORMATION FOR SEQ ID NO:14:

( i ) SEQUENCE CHARACTERISTICS:
                    ( A ) LENGTH: 27 nucleotides
                    ( B ) TYPE: nucleic acid
                    ( C ) STRANDEDNESS: single
                    ( D ) TOPOLOGY: linear ( i i ) MOLECULE TYPE: synthetic DNA ( x ) PUBLICATION INFORMATION:
                    ( A ) AUTHORS: Rudert, W.A.
                                   Trucco, M.
                    ( B ) TITLE: A Novel Approach to Rapid HLA Class II
                                 Molecular Typing
                    ( C ) JOURNAL: HLA 1991
                    ( D ) VOLUME: 2
                    ( F ) PAGES: 352-356
                    ( G ) DATE: 1992
                    ( K ) RELEVANT RESIDUES IN SEQ ID NO: 14: 1 to 27

( x i ) SEQUENCE DESCRIPTION: SEQ ID NO: 14:

GCCGAGATCT GGCCGCCTGA CGCCGAG                                    27

( 2 ) INFORMATION FOR SEQ ID NO:15:

( i ) SEQUENCE CHARACTERISTICS:
                    ( A ) LENGTH: 27 nucleotides
                    ( B ) TYPE: nucleic acid
                    ( C ) STRANDEDNESS: single
                    ( D ) TOPOLOGY: linear ( i i ) MOLECULE TYPE: synthetic DNA ( x ) PUBLICATION INFORMATION:
                    ( A ) AUTHORS: Rudert, W.A.
                                   Trucco, M.
                    ( B ) TITLE: A Novel Approach to Rapid HLA Class II
                                 Molecular Typing
                    ( C ) JOURNAL: HLA 1991
                    ( D ) VOLUME: 2
                    ( F ) PAGES: 352-356
                    ( G ) DATE: 1992
                    ( K ) RELEVANT RESIDUES IN SEQ ID NO: 15: 1 to 27

( x i ) SEQUENCE DESCRIPTION: SEQ ID NO: 15:

GCCGAGATCT GGCCGCCTGC CGCCGAG                                    27

( 2 ) INFORMATION FOR SEQ ID NO:16:

( i ) SEQUENCE CHARACTERISTICS:
                    ( A ) LENGTH: 27 nucleotides
                    ( B ) TYPE: nucleic acid
                    ( C ) STRANDEDNESS: single
                    ( D ) TOPOLOGY: linear ( i i ) MOLECULE TYPE: synthetic DNA ( x ) PUBLICATION INFORMATION:
                    ( A ) AUTHORS: Rudert, W.A.
                                   Trucco, M.

(B) TITLE: A Novel Approach to Rapid HLA Class II
    Molecular Typing
(C) JOURNAL: HLA 1991
(D) VOLUME: 2
(F) PAGES: 352-356
(G) DATE: 1992
(K) RELEVANT RESIDUES IN SEQ ID NO: 16: 1 to 27

(x i) SEQUENCE DESCRIPTION: SEQ ID NO: 16:

GCCGAGATCT GGCGGCTTGA CGCCGAG                    27

(2) INFORMATION FOR SEQ ID NO:17:

(i) SEQUENCE CHARACTERISTICS:
    (A) LENGTH: 27 nucleotides
    (B) TYPE: nucleic acid
    (C) STRANDEDNESS: single
    (D) TOPOLOGY: linear (ii) MOLECULE TYPE: synthetic DNA (x) PUBLICATION INFORMATION:
    (A) AUTHORS: Rudert, W.A.
        Trucco, M.
    (B) TITLE: A Novel Approach to Rapid HLA Class II
        Molecular Typing
    (C) JOURNAL: HLA 1991
    (D) VOLUME: 2
    (F) PAGES: 352-356
    (G) DATE: 1992
    (K) RELEVANT RESIDUES IN SEQ ID NO: 17: 1 to 27

(x i) SEQUENCE DESCRIPTION: SEQ ID NO: 17:

AACAGGCCGC CAGATCTCGG CAACAGG                    27

(2) INFORMATION FOR SEQ ID NO:18:

(i) SEQUENCE CHARACTERISTICS:
    (A) LENGTH: 27 nucleotides
    (B) TYPE: nucleic acid
    (C) STRANDEDNESS: single
    (D) TOPOLOGY: linear (ii) MOLECULE TYPE: synthetic DNA (x) PUBLICATION INFORMATION:
    (A) AUTHORS: Rudert, W.A.
        Trucco, M.
    (B) TITLE: A Novel Approach to Rapid HLA Class II
        Molecular Typing
    (C) JOURNAL: HLA 1991
    (D) VOLUME: 2
    (F) PAGES: 352-356
    (G) DATE: 1992
    (K) RELEVANT RESIDUES IN SEQ ID NO: 18: 1 to 27

(x i) SEQUENCE DESCRIPTION: SEQ ID NO: 18:

GCTAGGCCGC CAGATCTCGG CGCTAGG                    27

(2) INFORMATION FOR SEQ ID NO:19:

(i) SEQUENCE CHARACTERISTICS:
    (A) LENGTH: 27 nucleotides
    (B) TYPE: nucleic acid
    (C) STRANDEDNESS: single
    (D) TOPOLOGY: linear (ii) MOLECULE TYPE: synthetic DNA (x) PUBLICATION INFORMATION:
    (A) AUTHORS: Rudert, W.A.
        Trucco, M.
    (B) TITLE: A Novel Approach to Rapid HLA Class II
        Molecular Typing (C) JOURNAL: HLA 1991
(D) VOLUME: 2
(F) PAGES: 352-356
(G) DATE: 1992
(K) RELEVANT RESIDUES IN SEQ ID NO: 19: 1 to 27

(xi) SEQUENCE DESCRIPTION: SEQ ID NO: 19:

GTCAGGCCGC CAGATCTCGG CGTCAGG 27

(2) INFORMATION FOR SEQ ID NO:20:

(i) SEQUENCE CHARACTERISTICS:
(A) LENGTH: 27 nucleotides
(B) TYPE: nucleic acid
(C) STRANDEDNESS: single
(D) TOPOLOGY: linear (ii) MOLECULE TYPE: synthetic DNA (x) PUBLICATION INFORMATION:
(A) AUTHORS: Rudert, W.A.
   Trucco, M.
(B) TITLE: A Novel Approach to Rapid HLA Class II
   Molecular Typing
(C) JOURNAL: HLA 1991
(D) VOLUME: 2
(F) PAGES: 352-356
(G) DATE: 1992
(K) RELEVANT RESIDUES IN SEQ ID NO: 20: 1 to 27

(xi) SEQUENCE DESCRIPTION: SEQ ID NO: 20:

ATCAGGCCGC CAGATCTCGG CATCAGG 27

(2) INFORMATION FOR SEQ ID NO:21:

(i) SEQUENCE CHARACTERISTICS:
(A) LENGTH: 27 nucleotides
(B) TYPE: nucleic acid
(C) STRANDEDNESS: single
(D) TOPOLOGY: linear (ii) MOLECULE TYPE: synthetic DNA (x) PUBLICATION INFORMATION:
(A) AUTHORS: Rudert, W.A.
   Trucco, M.
(B) TITLE: A Novel Approach to Rapid HLA Class II
   Molecular Typing
(C) JOURNAL: HLA 1991
(D) VOLUME: 2
(F) PAGES: 352-356
(G) DATE: 1992
(K) RELEVANT RESIDUES IN SEQ ID NO: 21: 1 to 27

(xi) SEQUENCE DESCRIPTION: SEQ ID NO: 21:

GGCAGGCAGC CAGATCTCGG CGGCAGG 27

(2) INFORMATION FOR SEQ ID NO:22:

(i) SEQUENCE CHARACTERISTICS:
(A) LENGTH: 27 nucleotides
(B) TYPE: nucleic acid
(C) STRANDEDNESS: single
(D) TOPOLOGY: linear (ii) MOLECULE TYPE: synthetic DNA (x) PUBLICATION INFORMATION:
(A) AUTHORS: Rudert, W.A.
   Trucco, M.
(B) TITLE: A Novel Approach to Rapid HLA Class II
   Molecular Typing
(C) JOURNAL: HLA 1991
(D) VOLUME: 2

( F ) PAGES: 352-356
( G ) DATE: 1992
( K ) RELEVANT RESIDUES IN SEQ ID NO: 22: 1 to 27

( x i ) SEQUENCE DESCRIPTION: SEQ ID NO: 22:

GTCAGGCGGC CAGATCTCGG CGTCAGG 27

( 2 ) INFORMATION FOR SEQ ID NO:23:

( i ) SEQUENCE CHARACTERISTICS:
    ( A ) LENGTH: 27 nucleotides
    ( B ) TYPE: nucleic acid
    ( C ) STRANDEDNESS: single
    ( D ) TOPOLOGY: linear ( i i ) MOLECULE TYPE: synthetic DNA ( x ) PUBLICATION INFORMATION:
    ( A ) AUTHORS: Rudert, W.A.
         Trucco, M.
    ( B ) TITLE: A Novel Approach to Rapid HLA Class II
         Molecular Typing
    ( C ) JOURNAL: HLA 1991
    ( D ) VOLUME: 2
    ( F ) PAGES: 352-356
    ( G ) DATE: 1992
    ( K ) RELEVANT RESIDUES IN SEQ ID NO: 23: 1 to 27

( x i ) SEQUENCE DESCRIPTION: SEQ ID NO: 23:

GGCAGGCGGC CAGATCTCGG CGGCAGG 27

( 2 ) INFORMATION FOR SEQ ID NO:24:

( i ) SEQUENCE CHARACTERISTICS:
    ( A ) LENGTH: 27 nucleotides
    ( B ) TYPE: nucleic acid
    ( C ) STRANDEDNESS: single
    ( D ) TOPOLOGY: linear ( i i ) MOLECULE TYPE: synthetic DNA ( x ) PUBLICATION INFORMATION:
    ( A ) AUTHORS: Rudert, W.A.
         Trucco, M.
    ( B ) TITLE: A Novel Approach to Rapid HLA Class II
         Molecular Typing
    ( C ) JOURNAL: HLA 1991
    ( D ) VOLUME: 2
    ( F ) PAGES: 352-356
    ( G ) DATE: 1992
    ( K ) RELEVANT RESIDUES IN SEQ ID NO: 24: 1 to 27

( x i ) SEQUENCE DESCRIPTION: SEQ ID NO: 24:

GTCAAGCCGC CAGATCTCGG CGTCAAG 27

( 2 ) INFORMATION FOR SEQ ID NO:25:

( i ) SEQUENCE CHARACTERISTICS:
    ( A ) LENGTH: 35 nucleotides
    ( B ) TYPE: nucleic acid
    ( C ) STRANDEDNESS: single
    ( D ) TOPOLOGY: linear ( i i ) MOLECULE TYPE: synthetic DNA ( x ) PUBLICATION INFORMATION:
    ( A ) AUTHORS: Rudert, W.A.
         Trucco, M.
    ( B ) TITLE: A Novel Approach to Rapid HLA Class II
         Molecular Typing
    ( C ) JOURNAL: HLA 1991
    ( D ) VOLUME: 2
    ( F ) PAGES: 352-356
    ( G ) DATE: 1992

( K ) RELEVANT RESIDUES IN SEQ ID NO: 25: 1 to 35

( x i ) SEQUENCE DESCRIPTION: SEQ ID NO: 25:

ACTCGAGGGG TGTGACCAGA CACTCGAGGG GTGTG    35

( 2 ) INFORMATION FOR SEQ ID NO:26:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( i i ) MOLECULE TYPE: synthetic DNA ( x ) PUBLICATION INFORMATION:
        ( A ) AUTHORS: Rudert, W.A.
            Trucco, M.
        ( B ) TITLE: A Novel Approach to Rapid HLA Class II
            Molecular Typing
        ( C ) JOURNAL: HLA 1991
        ( D ) VOLUME: 2
        ( F ) PAGES: 352-356
        ( G ) DATE: 1992
        ( K ) RELEVANT RESIDUES IN SEQ ID NO: 26: 1 to 35

( x i ) SEQUENCE DESCRIPTION: SEQ ID NO: 26:

ACTCGAGTTA TGTGACCAGA TACTCGAGTT ATGTG    35

( 2 ) INFORMATION FOR SEQ ID NO:27:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( i i ) MOLECULE TYPE: synthetic DNA ( x ) PUBLICATION INFORMATION:
        ( A ) AUTHORS: Rudert, W.A.
            Trucco, M.
        ( B ) TITLE: A Novel Approach to Rapid HLA Class II
            Molecular Typing
        ( C ) JOURNAL: HLA 1991
        ( D ) VOLUME: 2
        ( F ) PAGES: 352-356
        ( G ) DATE: 1992
        ( K ) RELEVANT RESIDUES IN SEQ ID NO: 27: 1 to 35

( x i ) SEQUENCE DESCRIPTION: SEQ ID NO: 27:

ACTCGAGTCT TGTGACCAGA TACTCGAGTC TTGTG    35

( 2 ) INFORMATION FOR SEQ ID NO:28:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( i i ) MOLECULE TYPE: synthetic DNA ( x ) PUBLICATION INFORMATION:
        ( A ) AUTHORS: Rudert, W.A.
            Trucco, M.
        ( B ) TITLE: A Novel Approach to Rapid HLA Class II
            Molecular Typing
        ( C ) JOURNAL: HLA 1991
        ( D ) VOLUME: 2
        ( F ) PAGES: 352-356
        ( G ) DATE: 1992
        ( K ) RELEVANT RESIDUES IN SEQ ID NO: 28: 1 to 35

( x i ) SEQUENCE DESCRIPTION: SEQ ID NO: 28:

ACTCGAGTCT TGTAACCAGA CACTCGAGTC TTGTA                    35

( 2 ) INFORMATION FOR SEQ ID NO:29:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( i i ) MOLECULE TYPE: synthetic DNA ( x ) PUBLICATION INFORMATION:
        ( A ) AUTHORS: Rudert, W.A.
                Trucco, M.
        ( B ) TITLE: A Novel Approach to Rapid HLA Class II
                Molecular Typing
        ( C ) JOURNAL: HLA 1991
        ( D ) VOLUME: 2
        ( F ) PAGES: 352-356
        ( G ) DATE: 1992
        ( K ) RELEVANT RESIDUES IN SEQ ID NO: 29: 1 to 35

( x i ) SEQUENCE DESCRIPTION: SEQ ID NO: 29:

ACTCGAGTCT TGTAACCAGA TACTCGAGTC TTGTA                    35

( 2 ) INFORMATION FOR SEQ ID NO:30:

( i ) SEQUENCE CHARACTERISTICS:
        ( A ) LENGTH: 35 nucleotides
        ( B ) TYPE: nucleic acid
        ( C ) STRANDEDNESS: single
        ( D ) TOPOLOGY: linear ( i i ) MOLECULE TYPE: synthetic DNA ( x ) PUBLICATION INFORMATION:
        ( A ) AUTHORS: Rudert, W.A.
                Trucco, M.
        ( B ) TITLE: A Novel Approach to Rapid HLA Class II
                Molecular Typing
        ( C ) JOURNAL: HLA 1991
        ( D ) VOLUME: 2
        ( F ) PAGES: 352-356
        ( G ) DATE: 1992
        ( K ) RELEVANT RESIDUES IN SEQ ID NO: 30: 1 to 35

( x i ) SEQUENCE DESCRIPTION: SEQ ID NO: 30:

ACTCGAGGGG TGTGACCAGA TACTCGAGGG GTGTG                    35

( 2 ) INFORMATION FOR SEQ ID NO:31:

( i ) SEQUENCE CHARACTERISTICS:
        ( A ) LENGTH: 21 nucleotides
        ( B ) TYPE: nucleic acid
        ( C ) STRANDEDNESS: single
        ( D ) TOPOLOGY: linear ( i i ) MOLECULE TYPE: synthetic DNA ( x ) PUBLICATION INFORMATION:
        ( A ) AUTHORS: Rudert, W.A.
                Trucco, M.
        ( B ) TITLE: A Novel Approach to Rapid HLA Class II
                Molecular Typing
        ( C ) JOURNAL: HLA 1991
        ( D ) VOLUME: 2
        ( F ) PAGES: 352-356
        ( G ) DATE: 1992
        ( K ) RELEVANT RESIDUES IN SEQ ID NO: 31: 1 to 21

( x i ) SEQUENCE DESCRIPTION: SEQ ID NO: 31:

GTCTGGTCAC ACCCCTCGAG T    21

( 2 ) INFORMATION FOR SEQ ID NO:32:

( i ) SEQUENCE CHARACTERISTICS:
        ( A ) LENGTH: 21 nucleotides
        ( B ) TYPE: nucleic acid
        ( C ) STRANDEDNESS: single
        ( D ) TOPOLOGY: linear ( i i ) MOLECULE TYPE: synthetic DNA ( x ) PUBLICATION INFORMATION:
        ( A ) AUTHORS: Rudert, W.A.
            Trucco, M.
        ( B ) TITLE: A Novel Approach to Rapid HLA Class II
            Molecular Typing
        ( C ) JOURNAL: HLA 1991
        ( D ) VOLUME: 2
        ( F ) PAGES: 352-356
        ( G ) DATE: 1992
        ( K ) RELEVANT RESIDUES IN SEQ ID NO: 32: 1 to 21

( x i ) SEQUENCE DESCRIPTION: SEQ ID NO: 32:

ATCTGGTCAC ATAACTCGAG T    21

( 2 ) INFORMATION FOR SEQ ID NO:33:

( i ) SEQUENCE CHARACTERISTICS:
        ( A ) LENGTH: 21 nucleotides
        ( B ) TYPE: nucleic acid
        ( C ) STRANDEDNESS: single
        ( D ) TOPOLOGY: linear ( i i ) MOLECULE TYPE: synthetic DNA ( x ) PUBLICATION INFORMATION:
        ( A ) AUTHORS: Rudert, W.A.
            Trucco, M.
        ( B ) TITLE: A Novel Approach to Rapid HLA Class II
            Molecular Typing
        ( C ) JOURNAL: HLA 1991
        ( D ) VOLUME: 2
        ( F ) PAGES: 352-356
        ( G ) DATE: 1992
        ( K ) RELEVANT RESIDUES IN SEQ ID NO: 33: 1 to 21

( x i ) SEQUENCE DESCRIPTION: SEQ ID NO: 33:

ATCTGGTCAC AAGACTCGAG T    21

( 2 ) INFORMATION FOR SEQ ID NO:34:

( i ) SEQUENCE CHARACTERISTICS:
        ( A ) LENGTH: 21 nucleotides
        ( B ) TYPE: nucleic acid
        ( C ) STRANDEDNESS: single
        ( D ) TOPOLOGY: linear ( i i ) MOLECULE TYPE: synthetic DNA ( x ) PUBLICATION INFORMATION:
        ( A ) AUTHORS: Rudert, W.A.
            Trucco, M.
        ( B ) TITLE: A Novel Approach to Rapid HLA Class II
            Molecular Typing
        ( C ) JOURNAL: HLA 1991
        ( D ) VOLUME: 2
        ( F ) PAGES: 352-356
        ( G ) DATE: 1992
        ( K ) RELEVANT RESIDUES IN SEQ ID NO: 34: 1 to 21

( x i ) SEQUENCE DESCRIPTION: SEQ ID NO: 34:

GTCTGGTTAC AAGACTCGAG T    21

( 2 ) INFORMATION FOR SEQ ID NO:35:

( i ) SEQUENCE CHARACTERISTICS:
        ( A ) LENGTH: 21 nucleotides
        ( B ) TYPE: nucleic acid
        ( C ) STRANDEDNESS: single
        ( D ) TOPOLOGY: linear ( i i ) MOLECULE TYPE: synthetic DNA ( x ) PUBLICATION INFORMATION:
        ( A ) AUTHORS: Rudert, W.A.
              Trucco, M.
        ( B ) TITLE: A Novel Approach to Rapid HLA Class II
              Molecular Typing
        ( C ) JOURNAL: HLA 1991
        ( D ) VOLUME: 2
        ( F ) PAGES: 352-356
        ( G ) DATE: 1992
        ( K ) RELEVANT RESIDUES IN SEQ ID NO: 35: 1 to 21

( x i ) SEQUENCE DESCRIPTION: SEQ ID NO: 35:

ATCTGGTTAC AAGACTCGAG T                                  21

( 2 ) INFORMATION FOR SEQ ID NO:36:

( i ) SEQUENCE CHARACTERISTICS:
        ( A ) LENGTH: 21 nucleotides
        ( B ) TYPE: nucleic acid
        ( C ) STRANDEDNESS: single
        ( D ) TOPOLOGY: linear ( i i ) MOLECULE TYPE: synthetic DNA ( x ) PUBLICATION INFORMATION:
        ( A ) AUTHORS: Rudert, W.A.
              Trucco, M.
        ( B ) TITLE: A Novel Approach to Rapid HLA Class II
              Molecular Typing
        ( C ) JOURNAL: HLA 1991
        ( D ) VOLUME: 2
        ( F ) PAGES: 352-356
        ( G ) DATE: 1992
        ( K ) RELEVANT RESIDUES IN SEQ ID NO: 36: 1 to 21

( x i ) SEQUENCE DESCRIPTION: SEQ ID NO: 36:

ATCTGGTCAC ACCCCTCGAG T                                  21

( 2 ) INFORMATION FOR SEQ ID NO:37:

( i ) SEQUENCE CHARACTERISTICS:
        ( A ) LENGTH: 20 nucleotides
        ( B ) TYPE: nucleic acid
        ( C ) STRANDEDNESS: single
        ( D ) TOPOLOGY: linear ( i i ) MOLECULE TYPE: genomic DNA ( i v ) ANTI-SENSE: no ( x ) PUBLICATION INFORMATION:
        ( A ) AUTHORS: Kimura, A.
              Sasazuki, T.
        ( B ) TITLE: Eleventh International Histocompatibility
              Workshop Reference Protocol for the HLA-DNA-Typing
              Technique
        ( C ) JOURNAL: HLA 1991
        ( D ) VOLUME: 1
        ( F ) PAGES: 397-419
        ( G ) DATE: 1992
        ( K ) RELEVANT RESIDUES IN SEQ ID NO: 37: 1 to 20

( x i ) SEQUENCE DESCRIPTION: SEQ ID NO: 37:

TTCTTGTGGC AGCTTAAGTT                                    20

( 2 ) INFORMATION FOR SEQ ID NO:38:

( i ) SEQUENCE CHARACTERISTICS:
        ( A ) LENGTH: 20 nucleotides
        ( B ) TYPE: nucleic acid
        ( C ) STRANDEDNESS: single
        ( D ) TOPOLOGY: linear ( i i ) MOLECULE TYPE: genomic DNA ( i v ) ANTI-SENSE: yes ( x ) PUBLICATION INFORMATION:
        ( A ) AUTHORS: Kimura, A.
                  Sasazuki, T.
        ( B ) TITLE: Eleventh International Histocompatibility
            Workshop Reference Protocol for the HLA-DNA-Typing
            Technique
        ( C ) JOURNAL: HLA 1991
        ( D ) VOLUME: 1
        ( F ) PAGES: 397-419
        ( G ) DATE: 1992
        ( K ) RELEVANT RESIDUES IN SEQ ID NO: 38: 1 to 20

( x i ) SEQUENCE DESCRIPTION: SEQ ID NO: 38:

CCGCTGCACT GTGAAGCTCT                                                                      20

( 2 ) INFORMATION FOR SEQ ID NO:39:

( i ) SEQUENCE CHARACTERISTICS:
        ( A ) LENGTH: 21 nucleotides
        ( B ) TYPE: nucleic acid
        ( C ) STRANDEDNESS: single
        ( D ) TOPOLOGY: linear ( i i ) MOLECULE TYPE: genomic DNA ( i v ) ANTI-SENSE: no ( x ) PUBLICATION INFORMATION:
        ( A ) AUTHORS: Kimura, A.
                  Sasazuki, T.
        ( B ) TITLE: Eleventh International Histocompatibility
            Workshop Reference Protocol for the HLA-DNA-Typing
            Technique
        ( C ) JOURNAL: HLA 1991
        ( D ) VOLUME: 1
        ( F ) PAGES: 397-419
        ( G ) DATE: 1992
        ( K ) RELEVANT RESIDUES IN SEQ ID NO: 39: 1 to 21

( x i ) SEQUENCE DESCRIPTION: SEQ ID NO: 39:

TTCCTGTGGC AGCCTAAGAG G                                                              21

( 2 ) INFORMATION FOR SEQ ID NO:40:

( i ) SEQUENCE CHARACTERISTICS:
        ( A ) LENGTH: 20 nucleotides
        ( B ) TYPE: nucleic acid
        ( C ) STRANDEDNESS: single
        ( D ) TOPOLOGY: linear ( i i ) MOLECULE TYPE: genomic DNA ( i v ) ANTI-SENSE: yes ( x ) PUBLICATION INFORMATION:
        ( A ) AUTHORS: Kimura, A.
                  Sasazuki, T.
        ( B ) TITLE: Eleventh International Histocompatibility
            Workshop Reference Protocol for the HLA-DNA-Typing
            Technique
        ( C ) JOURNAL: HLA 1991
        ( D ) VOLUME: 1

( F ) PAGES: 397-419
( G ) DATE: 1992
( K ) RELEVANT RESIDUES IN SEQ ID NO: 40: 1 to 20

( x i ) SEQUENCE DESCRIPTION: SEQ ID NO: 40:

CCGCTGCACT GTGAAGCTCT 20

( 2 ) INFORMATION FOR SEQ ID NO:41:

( i ) SEQUENCE CHARACTERISTICS:
      ( A ) LENGTH: 21 nucleotides
      ( B ) TYPE: nucleic acid
      ( C ) STRANDEDNESS: single
      ( D ) TOPOLOGY: linear ( i i i ) MOLECULE TYPE: genomic DNA ( i v ) ANTI-SENSE: no ( x ) PUBLICATION INFORMATION:
      ( A ) AUTHORS: Kimura, A.
              Sasazuki, T.
      ( B ) TITLE: Eleventh International Histocompatibility
           Workshop Reference Protocol for the HLA-DNA-Typing
           Technique
      ( C ) JOURNAL: HLA 1991
      ( D ) VOLUME: 1
      ( F ) PAGES: 397-419
      ( G ) DATE: 1992
      ( K ) RELEVANT RESIDUES IN SEQ ID NO: 41: 1 to 21

( x i ) SEQUENCE DESCRIPTION: SEQ ID NO: 41:

GTTTCTTGGA GCAGGTTAAA C 21

( 2 ) INFORMATION FOR SEQ ID NO:42:

( i ) SEQUENCE CHARACTERISTICS:
      ( A ) LENGTH: 20 nucleotides
      ( B ) TYPE: nucleic acid
      ( C ) STRANDEDNESS: single
      ( D ) TOPOLOGY: linear ( i i i ) MOLECULE TYPE: genomic DNA ( i v ) ANTI-SENSE: yes ( x ) PUBLICATION INFORMATION:
      ( A ) AUTHORS: Kimura, A.
              Sasazuki, T.
      ( B ) TITLE: Eleventh International Histocompatibility
           Workshop Reference Protocol for the HLA-DNA-Typing
           Technique
      ( C ) JOURNAL: HLA 1991
      ( D ) VOLUME: 1
      ( F ) PAGES: 397-419
      ( G ) DATE: 1992
      ( K ) RELEVANT RESIDUES IN SEQ ID NO: 42: 1 to 20

( x i ) SEQUENCE DESCRIPTION: SEQ ID NO: 42:

CCGCTGCACT GTGAAGCTCT 20

( 2 ) INFORMATION FOR SEQ ID NO:43:

( i ) SEQUENCE CHARACTERISTICS:
      ( A ) LENGTH: 22 nucleotides
      ( B ) TYPE: nucleic acid
      ( C ) STRANDEDNESS: single
      ( D ) TOPOLOGY: linear ( i i i ) MOLECULE TYPE: genomic DNA ( i v ) ANTI-SENSE: no ( x ) PUBLICATION INFORMATION:

(A) AUTHORS: Kimura, A.
             Sasazuki, T.
(B) TITLE: Eleventh International Histocompatibility
           Workshop Reference Protocol for the HLA-DNA-Typing
           Technique
(C) JOURNAL: HLA 1991
(D) VOLUME: 1
(F) PAGES: 397-419
(G) DATE: 1992
(K) RELEVANT RESIDUES IN SEQ ID NO: 43: 1 to 22

(x i) SEQUENCE DESCRIPTION: SEQ ID NO: 43:

CACGTTTCTT GGAGTACTCT AC         22

(2) INFORMATION FOR SEQ ID NO:44:

(i) SEQUENCE CHARACTERISTICS:
    (A) LENGTH: 20 nucleotides
    (B) TYPE: nucleic acid
    (C) STRANDEDNESS: single
    (D) TOPOLOGY: linear (ii) MOLECULE TYPE: genomic DNA (iv) ANTI-SENSE: yes (x) PUBLICATION INFORMATION:
    (A) AUTHORS: Kimura, A.
                 Sasazuki, T.
    (B) TITLE: Eleventh International Histocompatibility
               Workshop Reference Protocol for the HLA-DNA-Typing
               Technique
    (C) JOURNAL: HLA 1991
    (D) VOLUME: 1
    (F) PAGES: 397-419
    (G) DATE: 1992
    (K) RELEVANT RESIDUES IN SEQ ID NO: 44: 1 to 20

(x i) SEQUENCE DESCRIPTION: SEQ ID NO: 44:

CCGCTGCACT GTGAAGCTCT            20

(2) INFORMATION FOR SEQ ID NO:45:

(i) SEQUENCE CHARACTERISTICS:
    (A) LENGTH: 21 nucleotides
    (B) TYPE: nucleic acid
    (C) STRANDEDNESS: single
    (D) TOPOLOGY: linear (ii) MOLECULE TYPE: genomic DNA (iv) ANTI-SENSE: no (x) PUBLICATION INFORMATION:
    (A) AUTHORS: Kimura, A.
                 Sasazuki, T.
    (B) TITLE: Eleventh International Histocompatibility
               Workshop Reference Protocol for the HLA-DNA-Typing
               Technique
    (C) JOURNAL: HLA 1991
    (D) VOLUME: 1
    (F) PAGES: 397-419
    (G) DATE: 1992
    (K) RELEVANT RESIDUES IN SEQ ID NO: 45: 1 to 21

(x i) SEQUENCE DESCRIPTION: SEQ ID NO: 45:

CCCAGCACGT TTCTTGGAGC T          21

(2) INFORMATION FOR SEQ ID NO:46:

(i) SEQUENCE CHARACTERISTICS:
    (A) LENGTH: 20 nucleotides
    (B) TYPE: nucleic acid
    (C) STRANDEDNESS: single (D) TOPOLOGY: linear (ii) MOLECULE TYPE: genomic DNA (iv) ANTI-SENSE: yes (x) PUBLICATION INFORMATION:
  (A) AUTHORS: Kimura, A.
      Sasazuki, T.
  (B) TITLE: Eleventh International Histocompatibility
      Workshop Reference Protocol for the HLA-DNA-Typing
      Technique
  (C) JOURNAL: HLA 1991
  (D) VOLUME: 1
  (F) PAGES: 397-419
  (G) DATE: 1992
  (K) RELEVANT RESIDUES IN SEQ ID NO: 46: 1 to 20

(xi) SEQUENCE DESCRIPTION: SEQ ID NO: 46:

CCGCTGCACT GTGAAGCTCT                        20

(2) INFORMATION FOR SEQ ID NO:47:

(i) SEQUENCE CHARACTERISTICS:
      (A) LENGTH: 18 nucleotides
      (B) TYPE: nucleic acid
      (C) STRANDEDNESS: single
      (D) TOPOLOGY: linear (ii) MOLECULE TYPE: genomic DNA (x) PUBLICATION INFORMATION:
      (A) AUTHORS: Kimura, A.
          Sasazuki, T.
      (B) TITLE: Eleventh International Histocompatibility
          Workshop Reference Protocol for the HLA-DNA-Typing
          Technique
      (C) JOURNAL: HLA 1991
      (D) VOLUME: 1
      (F) PAGES: 397-419
      (G) DATE: 1992
      (K) RELEVANT RESIDUES IN SEQ ID NO: 47: 1 to 18

(xi) SEQUENCE DESCRIPTION: SEQ ID NO: 47:

TAAGTTTGAA TGTCATTT                          18

(2) INFORMATION FOR SEQ ID NO:48:

(i) SEQUENCE CHARACTERISTICS:
      (A) LENGTH: 18 nucleotides
      (B) TYPE: nucleic acid
      (C) STRANDEDNESS: single
      (D) TOPOLOGY: linear (ii) MOLECULE TYPE: genomic DNA (x) PUBLICATION INFORMATION:
      (A) AUTHORS: Kimura, A.
          Sasazuki, T.
      (B) TITLE: Eleventh International Histocompatibility
          Workshop Reference Protocol for the HLA-DNA-Typing
          Technique
      (C) JOURNAL: HLA 1991
      (D) VOLUME: 1
      (F) PAGES: 397-419
      (G) DATE: 1992
      (K) RELEVANT RESIDUES IN SEQ ID NO: 48: 1 to 18

(xi) SEQUENCE DESCRIPTION: SEQ ID NO: 48:

CCTAAGAGGG AGTGTCAT                          18

(2) INFORMATION FOR SEQ ID NO:49:

(i) SEQUENCE CHARACTERISTICS:

(A) LENGTH: 18 nucleotides
(B) TYPE: nucleic acid
(C) STRANDEDNESS: single
(D) TOPOLOGY: linear (ii) MOLECULE TYPE: genomic DNA (x) PUBLICATION INFORMATION:
(A) AUTHORS: Kimura, A.
Sasazuki, T.
(B) TITLE: Eleventh International Histocompatibility
Workshop Reference Protocol for the HLA-DNA-Typing
Technique
(C) JOURNAL: HLA 1991
(D) VOLUME: 1
(F) PAGES: 397-419
(G) DATE: 1992
(K) RELEVANT RESIDUES IN SEQ ID NO: 49: 1 to 18

(xi) SEQUENCE DESCRIPTION: SEQ ID NO: 49:

GTACTCTACG TCTGAGTG  18

(2) INFORMATION FOR SEQ ID NO:50:

(i) SEQUENCE CHARACTERISTICS:
(A) LENGTH: 18 nucleotides
(B) TYPE: nucleic acid
(C) STRANDEDNESS: single
(D) TOPOLOGY: linear (ii) MOLECULE TYPE: genomic DNA (x) PUBLICATION INFORMATION:
(A) AUTHORS: Kimura, A.
Sasazuki, T.
(B) TITLE: Eleventh International Histocompatibility
Workshop Reference Protocol for the HLA-DNA-Typing
Technique
(C) JOURNAL: HLA 1991
(D) VOLUME: 1
(F) PAGES: 397-419
(G) DATE: 1992
(K) RELEVANT RESIDUES IN SEQ ID NO: 50: 1 to 18

(xi) SEQUENCE DESCRIPTION: SEQ ID NO: 50:

GAGCAGGTTA AACATGAG  18

(2) INFORMATION FOR SEQ ID NO:51:

(i) SEQUENCE CHARACTERISTICS:
(A) LENGTH: 18 nucleotides
(B) TYPE: nucleic acid
(C) STRANDEDNESS: single
(D) TOPOLOGY: linear (ii) MOLECULE TYPE: genomic DNA (x) PUBLICATION INFORMATION:
(A) AUTHORS: Kimura, A.
Sasazuki, T.
(B) TITLE: Eleventh International Histocompatibility
Workshop Reference Protocol for the HLA-DNA-Typing
Technique
(C) JOURNAL: HLA 1991
(D) VOLUME: 1
(F) PAGES: 397-419
(G) DATE: 1992
(K) RELEVANT RESIDUES IN SEQ ID NO: 51: 1 to 18

(xi) SEQUENCE DESCRIPTION: SEQ ID NO: 51:

AGAAATAACA CTCACCCG  18

(2) INFORMATION FOR SEQ ID NO:52:

( i ) SEQUENCE CHARACTERISTICS:
    ( A ) LENGTH: 18 nucleotides
    ( B ) TYPE: nucleic acid
    ( C ) STRANDEDNESS: single
    ( D ) TOPOLOGY: linear ( i i ) MOLECULE TYPE: genomic DNA ( x ) PUBLICATION INFORMATION:
    ( A ) AUTHORS: Kimura, A.
                    Sasazuki, T.
    ( B ) TITLE: Eleventh International Histocompatibility
           Workshop Reference Protocol for the HLA-DNA-Typing
           Technique
    ( C ) JOURNAL: HLA 1991
    ( D ) VOLUME: 1
    ( F ) PAGES: 397-419
    ( G ) DATE: 1992
    ( K ) RELEVANT RESIDUES IN SEQ ID NO: 52: 1 to 18

( x i ) SEQUENCE DESCRIPTION: SEQ ID NO: 52:

TGGCAGGGTA AGTATAAG                                            18

( 2 ) INFORMATION FOR SEQ ID NO:53:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( x ) PUBLICATION INFORMATION:
        ( A ) AUTHORS: Kimura, A.
                    Sasazuki, T.
        ( B ) TITLE: Eleventh International Histocompatibility
                Workshop Reference Protocol for the HLA-DNA-Typing
                Technique
        ( C ) JOURNAL: HLA 1991
        ( D ) VOLUME: 1
        ( F ) PAGES: 397-419
        ( G ) DATE: 1992
        ( K ) RELEVANT RESIDUES IN SEQ ID NO: 53: 1 to 18

( x i ) SEQUENCE DESCRIPTION: SEQ ID NO: 53:

GAAGCAGGAT AAGTTTGA                                            18

( 2 ) INFORMATION FOR SEQ ID NO:54:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( x ) PUBLICATION INFORMATION:
        ( A ) AUTHORS: Kimura, A.
                    Sasazuki, T.
        ( B ) TITLE: Eleventh International Histocompatibility
                Workshop Reference Protocol for the HLA-DNA-Typing
                Technique
        ( C ) JOURNAL: HLA 1991
        ( D ) VOLUME: 1
        ( F ) PAGES: 397-419
        ( G ) DATE: 1992
        ( K ) RELEVANT RESIDUES IN SEQ ID NO: 54: 1 to 18

( x i ) SEQUENCE DESCRIPTION: SEQ ID NO: 54:

GAGGAGGTTA AGTTTGAG                                            18

( 2 ) INFORMATION FOR SEQ ID NO:55:

( i ) SEQUENCE CHARACTERISTICS:
    ( A ) LENGTH: 18 nucleotides
    ( B ) TYPE: nucleic acid
    ( C ) STRANDEDNESS: single
    ( D ) TOPOLOGY: linear ( i i ) MOLECULE TYPE: genomic DNA ( x ) PUBLICATION INFORMATION:
    ( A ) AUTHORS: Kimura, A.
              Sasazuki, T.
    ( B ) TITLE: Eleventh International Histocompatibility
              Workshop Reference Protocol for the HLA-DNA-Typing
              Technique
    ( C ) JOURNAL: HLA 1991
    ( D ) VOLUME: 1
    ( F ) PAGES: 397-419
    ( G ) DATE: 1992
    ( K ) RELEVANT RESIDUES IN SEQ ID NO: 55: 1 to 18

( x i ) SEQUENCE DESCRIPTION: SEQ ID NO: 55:

CAGCAGGATA AGTATGAG                                                                18

( 2 ) INFORMATION FOR SEQ ID NO:56:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( x ) PUBLICATION INFORMATION:
        ( A ) AUTHORS: Kimura, A.
                  Sasazuki, T.
        ( B ) TITLE: Eleventh International Histocompatibility
                  Workshop Reference Protocol for the HLA-DNA-Typing
                  Technique
        ( C ) JOURNAL: HLA 1991
        ( D ) VOLUME: 1
        ( F ) PAGES: 397-419
        ( G ) DATE: 1992
        ( K ) RELEVANT RESIDUES IN SEQ ID NO: 56: 1 to 18

( x i ) SEQUENCE DESCRIPTION: SEQ ID NO: 56:

GAGCTGCGTA AGTCTGAG                                                                18

( 2 ) INFORMATION FOR SEQ ID NO:57:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( x ) PUBLICATION INFORMATION:
        ( A ) AUTHORS: Kimura, A.
                  Sasazuki, T.
        ( B ) TITLE: Eleventh International Histocompatibility
                  Workshop Reference Protocol for the HLA-DNA-Typing
                  Technique
        ( C ) JOURNAL: HLA 1991
        ( D ) VOLUME: 1
        ( F ) PAGES: 397-419
        ( G ) DATE: 1992
        ( K ) RELEVANT RESIDUES IN SEQ ID NO: 57: 1 to 18

( x i ) SEQUENCE DESCRIPTION: SEQ ID NO: 57:

GAGCTGCTTA AGTCTGAG                                                                18

( 2 ) INFORMATION FOR SEQ ID NO:58:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( x ) PUBLICATION INFORMATION:
        ( A ) AUTHORS: Kimura, A.
                Sasazuki, T.
        ( B ) TITLE: Eleventh International Histocompatibility
               Workshop Reference Protocol for the HLA-DNA-Typing
               Technique
        ( C ) JOURNAL: HLA 1991
        ( D ) VOLUME: 1
        ( F ) PAGES: 397-419
        ( G ) DATE: 1992
        ( K ) RELEVANT RESIDUES IN SEQ ID NO: 58: 1 to 18

( x i ) SEQUENCE DESCRIPTION: SEQ ID NO: 58:

GAGCAGGCTA AGTGTGAG                                                    18

( 2 ) INFORMATION FOR SEQ ID NO:59:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( x ) PUBLICATION INFORMATION:
        ( A ) AUTHORS: Kimura, A.
                Sasazuki, T.
        ( B ) TITLE: Eleventh International Histocompatibility
               Workshop Reference Protocol for the HLA-DNA-Typing
               Technique
        ( C ) JOURNAL: HLA 1991
        ( D ) VOLUME: 1
        ( F ) PAGES: 397-419
        ( G ) DATE: 1992
        ( K ) RELEVANT RESIDUES IN SEQ ID NO: 59: 1 to 18

( x i ) SEQUENCE DESCRIPTION: SEQ ID NO: 59:

TCTGAGTGTC AATTCTTC                                                    18

( 2 ) INFORMATION FOR SEQ ID NO:60:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( x ) PUBLICATION INFORMATION:
        ( A ) AUTHORS: Kimura, A.
                Sasazuki, T.
        ( B ) TITLE: Eleventh International Histocompatibility
               Workshop Reference Protocol for the HLA-DNA-Typing
               Technique
        ( C ) JOURNAL: HLA 1991
        ( D ) VOLUME: 1
        ( F ) PAGES: 397-419
        ( G ) DATE: 1992
        ( K ) RELEVANT RESIDUES IN SEQ ID NO: 60: 1 to 18

( x i ) SEQUENCE DESCRIPTION: SEQ ID NO: 60:

AACTACGGGG TTGGTGAG                                                    18

( 2 ) INFORMATION FOR SEQ ID NO:61:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( x ) PUBLICATION INFORMATION:
        ( A ) AUTHORS: Kimura, A.
                       Sasazuki, T.
        ( B ) TITLE: Eleventh International Histocompatibility
               Workshop Reference Protocol for the HLA-DNA-Typing
               Technique
        ( C ) JOURNAL: HLA 1991
        ( D ) VOLUME: 1
        ( F ) PAGES: 397-419
        ( G ) DATE: 1992
        ( K ) RELEVANT RESIDUES IN SEQ ID NO: 61: 1 to 18

( x i ) SEQUENCE DESCRIPTION: SEQ ID NO: 61:

AACTACGGGG CTGTGGAG                                              18

( 2 ) INFORMATION FOR SEQ ID NO:62:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( x ) PUBLICATION INFORMATION:
        ( A ) AUTHORS: Kimura, A.
                       Sasazuki, T.
        ( B ) TITLE: Eleventh International Histocompatibility
               Workshop Reference Protocol for the HLA-DNA-Typing
               Technique
        ( C ) JOURNAL: HLA 1991
        ( D ) VOLUME: 1
        ( F ) PAGES: 397-419
        ( G ) DATE: 1992
        ( K ) RELEVANT RESIDUES IN SEQ ID NO: 62: 1 to 18

( x i ) SEQUENCE DESCRIPTION: SEQ ID NO: 62:

AACTACGGGG TTGTGGAG                                              18

( 2 ) INFORMATION FOR SEQ ID NO:63:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( x ) PUBLICATION INFORMATION:
        ( A ) AUTHORS: Kimura, A.
                       Sasazuki, T.
        ( B ) TITLE: Eleventh International Histocompatibility
               Workshop Reference Protocol for the HLA-DNA-Typing
               Technique
        ( C ) JOURNAL: HLA 1991
        ( D ) VOLUME: 1
        ( F ) PAGES: 397-419
        ( G ) DATE: 1992
        ( K ) RELEVANT RESIDUES IN SEQ ID NO: 63: 1 to 18

( x i ) SEQUENCE DESCRIPTION: SEQ ID NO: 63:

GCCTGATGCC GAGTACTG                                              18

( 2 ) INFORMATION FOR SEQ ID NO:64:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( x ) PUBLICATION INFORMATION:
        ( A ) AUTHORS: Kimura, A.
                     Sasazuki, T.
        ( B ) TITLE: Eleventh International Histocompatibility
                  Workshop Reference Protocol for the HLA-DNA-Typing
                  Technique
        ( C ) JOURNAL: HLA 1991
        ( D ) VOLUME: 1
        ( F ) PAGES: 397-419
        ( G ) DATE: 1992
        ( K ) RELEVANT RESIDUES IN SEQ ID NO: 64: 1 to 18

( x i ) SEQUENCE DESCRIPTION: SEQ ID NO: 64:

GCCTAGCGCC GAGTACTG                                                  18

( 2 ) INFORMATION FOR SEQ ID NO:65:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( x ) PUBLICATION INFORMATION:
        ( A ) AUTHORS: Kimura, A.
                     Sasazuki, T.
        ( B ) TITLE: Eleventh International Histocompatibility
                  Workshop Reference Protocol for the HLA-DNA-Typing
                  Technique
        ( C ) JOURNAL: HLA 1991
        ( D ) VOLUME: 1
        ( F ) PAGES: 397-419
        ( G ) DATE: 1992
        ( K ) RELEVANT RESIDUES IN SEQ ID NO: 65: 1 to 18

( x i ) SEQUENCE DESCRIPTION: SEQ ID NO: 65:

GCCTGATGAG GAGTACTG                                                  18

( 2 ) INFORMATION FOR SEQ ID NO:66:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( x ) PUBLICATION INFORMATION:
        ( A ) AUTHORS: Kimura, A.
                     Sasazuki, T.
        ( B ) TITLE: Eleventh International Histocompatibility
                  Workshop Reference Protocol for the HLA-DNA-Typing
                  Technique
        ( C ) JOURNAL: HLA 1991
        ( D ) VOLUME: 1
        ( F ) PAGES: 397-419
        ( G ) DATE: 1992
        ( K ) RELEVANT RESIDUES IN SEQ ID NO: 66: 1 to 18

( x i ) SEQUENCE DESCRIPTION: SEQ ID NO: 66:

GCCTGCTGCG GAGCACTG      18

(2) INFORMATION FOR SEQ ID NO:67:

(i) SEQUENCE CHARACTERISTICS:
    (A) LENGTH: 18 nucleotides
    (B) TYPE: nucleic acid
    (C) STRANDEDNESS: single
    (D) TOPOLOGY: linear (ii) MOLECULE TYPE: genomic DNA (x) PUBLICATION INFORMATION:
    (A) AUTHORS: Kimura, A.
                 Sasazuki, T.
    (B) TITLE: Eleventh International Histocompatibility
               Workshop Reference Protocol for the HLA-DNA-Typing
               Technique
    (C) JOURNAL: HLA 1991
    (D) VOLUME: 1
    (F) PAGES: 397-419
    (G) DATE: 1992
    (K) RELEVANT RESIDUES IN SEQ ID NO: 67: 1 to 18

(xi) SEQUENCE DESCRIPTION: SEQ ID NO: 67:

GCCTGTCGCC GAGTCCTG      18

(2) INFORMATION FOR SEQ ID NO:68:

(i) SEQUENCE CHARACTERISTICS:
    (A) LENGTH: 18 nucleotides
    (B) TYPE: nucleic acid
    (C) STRANDEDNESS: single
    (D) TOPOLOGY: linear (ii) MOLECULE TYPE: genomic DNA (x) PUBLICATION INFORMATION:
    (A) AUTHORS: Kimura, A.
                 Sasazuki, T.
    (B) TITLE: Eleventh International Histocompatibility
               Workshop Reference Protocol for the HLA-DNA-Typing
               Technique
    (C) JOURNAL: HLA 1991
    (D) VOLUME: 1
    (F) PAGES: 397-419
    (G) DATE: 1992
    (K) RELEVANT RESIDUES IN SEQ ID NO: 68: 1 to 18

(xi) SEQUENCE DESCRIPTION: SEQ ID NO: 68:

GCCTGACGCT GAGTACTG      18

(2) INFORMATION FOR SEQ ID NO:69:

(i) SEQUENCE CHARACTERISTICS:
    (A) LENGTH: 18 nucleotides
    (B) TYPE: nucleic acid
    (C) STRANDEDNESS: single
    (D) TOPOLOGY: linear (ii) MOLECULE TYPE: genomic DNA (x) PUBLICATION INFORMATION:
    (A) AUTHORS: Kimura, A.
                 Sasazuki, T.
    (B) TITLE: Eleventh International Histocompatibility
               Workshop Reference Protocol for the HLA-DNA-Typing
               Technique
    (C) JOURNAL: HLA 1991
    (D) VOLUME: 1
    (F) PAGES: 397-419
    (G) DATE: 1992
    (K) RELEVANT RESIDUES IN SEQ ID NO: 69: 1 to 18

(xi) SEQUENCE DESCRIPTION: SEQ ID NO: 69:

GCCTGACGCC GAGTACTG 18

(2) INFORMATION FOR SEQ ID NO:70:

(i) SEQUENCE CHARACTERISTICS:
        (A) LENGTH: 18 nucleotides
        (B) TYPE: nucleic acid
        (C) STRANDEDNESS: single
        (D) TOPOLOGY: linear (ii) MOLECULE TYPE: genomic DNA (x) PUBLICATION INFORMATION:
        (A) AUTHORS: Kimura, A.
                    Sasazuki, T.
        (B) TITLE: Eleventh International Histocompatibility
              Workshop Reference Protocol for the HLA-DNA-Typing
              Technique
        (C) JOURNAL: HLA 1991
        (D) VOLUME: 1
        (F) PAGES: 397-419
        (G) DATE: 1992
        (K) RELEVANT RESIDUES IN SEQ ID NO: 70: 1 to 18

(xi) SEQUENCE DESCRIPTION: SEQ ID NO: 70:

GCCTGATGCT GAGTACTG 18

(2) INFORMATION FOR SEQ ID NO:71:

(i) SEQUENCE CHARACTERISTICS:
        (A) LENGTH: 18 nucleotides
        (B) TYPE: nucleic acid
        (C) STRANDEDNESS: single
        (D) TOPOLOGY: linear (ii) MOLECULE TYPE: genomic DNA (x) PUBLICATION INFORMATION:
        (A) AUTHORS: Kimura, A.
                    Sasazuki, T.
        (B) TITLE: Eleventh International Histocompatibility
              Workshop Reference Protocol for the HLA-DNA-Typing
              Technique
        (C) JOURNAL: HLA 1991
        (D) VOLUME: 1
        (F) PAGES: 397-419
        (G) DATE: 1992
        (K) RELEVANT RESIDUES IN SEQ ID NO: 71: 1 to 18

(xi) SEQUENCE DESCRIPTION: SEQ ID NO: 71:

GCCTGTTGCC GAGTCCTG 18

(2) INFORMATION FOR SEQ ID NO:72:

(i) SEQUENCE CHARACTERISTICS:
        (A) LENGTH: 18 nucleotides
        (B) TYPE: nucleic acid
        (C) STRANDEDNESS: single
        (D) TOPOLOGY: linear (ii) MOLECULE TYPE: genomic DNA (x) PUBLICATION INFORMATION:
        (A) AUTHORS: Kimura, A.
                    Sasazuki, T.
        (B) TITLE: Eleventh International Histocompatibility
              Workshop Reference Protocol for the HLA-DNA-Typing
              Technique
        (C) JOURNAL: HLA 1991
        (D) VOLUME: 1
        (F) PAGES: 397-419
        (G) DATE: 1992
        (K) RELEVANT RESIDUES IN SEQ ID NO: 72: 1 to 18

(xi) SEQUENCE DESCRIPTION: SEQ ID NO: 72:

CGGTTGCTGG AAAGATGC                                                                18

( 2 ) INFORMATION FOR SEQ ID NO:73:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( x ) PUBLICATION INFORMATION:
        ( A ) AUTHORS: Kimura, A.
                Sasazuki, T.
        ( B ) TITLE: Eleventh International Histocompatibility
               Workshop Reference Protocol for the HLA-DNA-Typing
               Technique
        ( C ) JOURNAL: HLA 1991
        ( D ) VOLUME: 1
        ( F ) PAGES: 397-419
        ( G ) DATE: 1992
        ( K ) RELEVANT RESIDUES IN SEQ ID NO: 73: 1 to 18

( x i ) SEQUENCE DESCRIPTION: SEQ ID NO: 73:

GGTTACTGGA GAGACACT                                                                18

( 2 ) INFORMATION FOR SEQ ID NO:74:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( x ) PUBLICATION INFORMATION:
        ( A ) AUTHORS: Kimura, A.
                Sasazuki, T.
        ( B ) TITLE: Eleventh International Histocompatibility
               Workshop Reference Protocol for the HLA-DNA-Typing
               Technique
        ( C ) JOURNAL: HLA 1991
        ( D ) VOLUME: 1
        ( F ) PAGES: 397-419
        ( G ) DATE: 1992
        ( K ) RELEVANT RESIDUES IN SEQ ID NO: 74: 1 to 18

( x i ) SEQUENCE DESCRIPTION: SEQ ID NO: 74:

TGGAAAGACT CTTCTATA                                                                18

( 2 ) INFORMATION FOR SEQ ID NO:75:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( x ) PUBLICATION INFORMATION:
        ( A ) AUTHORS: Kimura, A.
                Sasazuki, T.
        ( B ) TITLE: Eleventh International Histocompatibility
               Workshop Reference Protocol for the HLA-DNA-Typing
               Technique
        ( C ) JOURNAL: HLA 1991
        ( D ) VOLUME: 1
        ( F ) PAGES: 397-419
        ( G ) DATE: 1992
        ( K ) RELEVANT RESIDUES IN SEQ ID NO: 75: 1 to 18

( x i ) SEQUENCE DESCRIPTION: SEQ ID NO: 75:

GTATCTGCAC AGAGGCAT 18

( 2 ) INFORMATION FOR SEQ ID NO:76:

( i ) SEQUENCE CHARACTERISTICS:
  ( A ) LENGTH: 18 nucleotides
  ( B ) TYPE: nucleic acid
  ( C ) STRANDEDNESS: single
  ( D ) TOPOLOGY: linear ( i i ) MOLECULE TYPE: genomic DNA ( x ) PUBLICATION INFORMATION:
  ( A ) AUTHORS: Kimura, A.
   Sasazuki, T.
  ( B ) TITLE: Eleventh International Histocompatibility
   Workshop Reference Protocol for the HLA-DNA-Typing
   Technique
  ( C ) JOURNAL: HLA 1991
  ( D ) VOLUME: 1
  ( F ) PAGES: 397-419
  ( G ) DATE: 1992
  ( K ) RELEVANT RESIDUES IN SEQ ID NO: 76: 1 to 18

( x i ) SEQUENCE DESCRIPTION: SEQ ID NO: 76:

GTTCCTGCAC AGAGACAT 18

( 2 ) INFORMATION FOR SEQ ID NO:77:

( i ) SEQUENCE CHARACTERISTICS:
  ( A ) LENGTH: 18 nucleotides
  ( B ) TYPE: nucleic acid
  ( C ) STRANDEDNESS: single
  ( D ) TOPOLOGY: linear ( i i ) MOLECULE TYPE: genomic DNA ( x ) PUBLICATION INFORMATION:
  ( A ) AUTHORS: Kimura, A.
   Sasazuki, T.
  ( B ) TITLE: Eleventh International Histocompatibility
   Workshop Reference Protocol for the HLA-DNA-Typing
   Technique
  ( C ) JOURNAL: HLA 1991
  ( D ) VOLUME: 1
  ( F ) PAGES: 397-419
  ( G ) DATE: 1992
  ( K ) RELEVANT RESIDUES IN SEQ ID NO: 77: 1 to 18

( x i ) SEQUENCE DESCRIPTION: SEQ ID NO: 77:

GTTCCTGCAC AGAGGCAT 18

( 2 ) INFORMATION FOR SEQ ID NO:78:

( i ) SEQUENCE CHARACTERISTICS:
  ( A ) LENGTH: 18 nucleotides
  ( B ) TYPE: nucleic acid
  ( C ) STRANDEDNESS: single
  ( D ) TOPOLOGY: linear ( i i ) MOLECULE TYPE: genomic DNA ( x ) PUBLICATION INFORMATION:
  ( A ) AUTHORS: Kimura, A.
   Sasazuki, T.
  ( B ) TITLE: Eleventh International Histocompatibility
   Workshop Reference Protocol for the HLA-DNA-Typing
   Technique
  ( C ) JOURNAL: HLA 1991
  ( D ) VOLUME: 1
  ( F ) PAGES: 397-419
  ( G ) DATE: 1992
  ( K ) RELEVANT RESIDUES IN SEQ ID NO: 78: 1 to 18

( x i ) SEQUENCE DESCRIPTION: SEQ ID NO: 78:

GCGGTACCTG GACAGATA 18

( 2 ) INFORMATION FOR SEQ ID NO:79:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( x ) PUBLICATION INFORMATION:
        ( A ) AUTHORS: Kimura, A.
                Sasazuki, T.
        ( B ) TITLE: Eleventh International Histocompatibility
                Workshop Reference Protocol for the HLA-DNA-Typing
                Technique
        ( C ) JOURNAL: HLA 1991
        ( D ) VOLUME: 1
        ( F ) PAGES: 397-419
        ( G ) DATE: 1992
        ( K ) RELEVANT RESIDUES IN SEQ ID NO: 79: 1 to 18

( x i ) SEQUENCE DESCRIPTION: SEQ ID NO: 79:

GTTCCTGGAG AGACACTT 18

( 2 ) INFORMATION FOR SEQ ID NO:80:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( x ) PUBLICATION INFORMATION:
        ( A ) AUTHORS: Kimura, A.
                Sasazuki, T.
        ( B ) TITLE: Eleventh International Histocompatibility
                Workshop Reference Protocol for the HLA-DNA-Typing
                Technique
        ( C ) JOURNAL: HLA 1991
        ( D ) VOLUME: 1
        ( F ) PAGES: 397-419
        ( G ) DATE: 1992
        ( K ) RELEVANT RESIDUES IN SEQ ID NO: 80: 1 to 18

( x i ) SEQUENCE DESCRIPTION: SEQ ID NO: 80:

TTCCTGGAGA GATACTTC 18

( 2 ) INFORMATION FOR SEQ ID NO:81:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( x ) PUBLICATION INFORMATION:
        ( A ) AUTHORS: Kimura, A.
                Sasazuki, T.
        ( B ) TITLE: Eleventh International Histocompatibility
                Workshop Reference Protocol for the HLA-DNA-Typing
                Technique
        ( C ) JOURNAL: HLA 1991
        ( D ) VOLUME: 1
        ( F ) PAGES: 397-419
        ( G ) DATE: 1992

( K ) RELEVANT RESIDUES IN SEQ ID NO: 81: 1 to 18

( x i ) SEQUENCE DESCRIPTION: SEQ ID NO: 81:

GCGAGTGTGG AACCTGAT 18

( 2 ) INFORMATION FOR SEQ ID NO:82:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( x ) PUBLICATION INFORMATION:
        ( A ) AUTHORS: Kimura, A.
                Sasazuki, T.
        ( B ) TITLE: Eleventh International Histocompatibility
              Workshop Reference Protocol for the HLA-DNA-Typing
              Technique
        ( C ) JOURNAL: HLA 1991
        ( D ) VOLUME: 1
        ( F ) PAGES: 397-419
        ( G ) DATE: 1992
        ( K ) RELEVANT RESIDUES IN SEQ ID NO: 82: 1 to 18

( x i ) SEQUENCE DESCRIPTION: SEQ ID NO: 82:

GCGAGTCTGG AACCTGAT 18

( 2 ) INFORMATION FOR SEQ ID NO:83:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( x ) PUBLICATION INFORMATION:
        ( A ) AUTHORS: Kimura, A.
                Sasazuki, T.
        ( B ) TITLE: Eleventh International Histocompatibility
              Workshop Reference Protocol for the HLA-DNA-Typing
              Technique
        ( C ) JOURNAL: HLA 1991
        ( D ) VOLUME: 1
        ( F ) PAGES: 397-419
        ( G ) DATE: 1992
        ( K ) RELEVANT RESIDUES IN SEQ ID NO: 83: 1 to 18

( x i ) SEQUENCE DESCRIPTION: SEQ ID NO: 83:

AAGTATCTCT CCAGGAAC 18

( 2 ) INFORMATION FOR SEQ ID NO:84:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( x ) PUBLICATION INFORMATION:
        ( A ) AUTHORS: Kimura, A.
                Sasazuki, T.
        ( B ) TITLE: Eleventh International Histocompatibility
              Workshop Reference Protocol for the HLA-DNA-Typing
              Technique
        ( C ) JOURNAL: HLA 1991
        ( D ) VOLUME: 1
        ( F ) PAGES: 397-419

(G) DATE: 1992
(K) RELEVANT RESIDUES IN SEQ ID NO: 84: 1 to 18

(x i) SEQUENCE DESCRIPTION: SEQ ID NO: :84:

GTTCCTGGAC AGATACTT 18

(2) INFORMATION FOR SEQ ID NO:85:

(i) SEQUENCE CHARACTERISTICS:
(A) LENGTH: 18 nucleotides
(B) TYPE: nucleic acid
(C) STRANDEDNESS: single
(D) TOPOLOGY: linear (i i) MOLECULE TYPE: genomic DNA (x) PUBLICATION INFORMATION:
(A) AUTHORS: Kimura, A.
Sasazuki, T.
(B) TITLE: Eleventh International Histocompatibility
Workshop Reference Protocol for the HLA-DNA-Typing
Technique
(C) JOURNAL: HLA 1991
(D) VOLUME: 1
(F) PAGES: 397-419
(G) DATE: 1992
(K) RELEVANT RESIDUES IN SEQ ID NO: 85: 1 to 18

(x i) SEQUENCE DESCRIPTION: SEQ ID NO: 85:

TCCTGGAGCA GAGGCGGG 18

(2) INFORMATION FOR SEQ ID NO:86:

(i) SEQUENCE CHARACTERISTICS:
(A) LENGTH: 18 nucleotides
(B) TYPE: nucleic acid
(C) STRANDEDNESS: single
(D) TOPOLOGY: linear (i i) MOLECULE TYPE: genomic DNA (x) PUBLICATION INFORMATION:
(A) AUTHORS: Kimura, A.
Sasazuki, T.
(B) TITLE: Eleventh International Histocompatibility
Workshop Reference Protocol for the HLA-DNA-Typing
Technique
(C) JOURNAL: HLA 1991
(D) VOLUME: 1
(F) PAGES: 397-419
(G) DATE: 1992
(K) RELEVANT RESIDUES IN SEQ ID NO: 86: 1 to 18

(x i) SEQUENCE DESCRIPTION: SEQ ID NO: 86:

GACTTCCTGG AAGACAGG 18

(2) INFORMATION FOR SEQ ID NO:87:

(i) SEQUENCE CHARACTERISTICS:
(A) LENGTH: 18 nucleotides
(B) TYPE: nucleic acid
(C) STRANDEDNESS: single
(D) TOPOLOGY: linear (i i) MOLECULE TYPE: genomic DNA (x) PUBLICATION INFORMATION:
(A) AUTHORS: Kimura, A.
Sasazuki, T.
(B) TITLE: Eleventh International Histocompatibility
Workshop Reference Protocol for the HLA-DNA-Typing
Technique
(C) JOURNAL: HLA 1991
(D) VOLUME: 1

(F) PAGES: 397-419
                (G) DATE: 1992
                (K) RELEVANT RESIDUES IN SEQ ID NO: 87: 1 to 18

(xi) SEQUENCE DESCRIPTION: SEQ ID NO: 87:

GACCTCCTGG AAGACAGG                                                                                    18

(2) INFORMATION FOR SEQ ID NO:88:

(i) SEQUENCE CHARACTERISTICS:
                (A) LENGTH: 18 nucleotides
                (B) TYPE: nucleic acid
                (C) STRANDEDNESS: single
                (D) TOPOLOGY: linear (ii) MOLECULE TYPE: genomic DNA (x) PUBLICATION INFORMATION:
                (A) AUTHORS: Kimura, A.
                             Sasazuki, T.
                (B) TITLE: Eleventh International Histocompatibility
                        Workshop Reference Protocol for the HLA-DNA-Typing
                        Technique
                (C) JOURNAL: HLA 1991
                (D) VOLUME: 1
                (F) PAGES: 397-419
                (G) DATE: 1992
                (K) RELEVANT RESIDUES IN SEQ ID NO: 88: 1 to 18

(xi) SEQUENCE DESCRIPTION: SEQ ID NO: 88:

GGCCGGGTGG ACAACTAC                                                                                    18

(2) INFORMATION FOR SEQ ID NO:89:

(i) SEQUENCE CHARACTERISTICS:
                (A) LENGTH: 18 nucleotides
                (B) TYPE: nucleic acid
                (C) STRANDEDNESS: single
                (D) TOPOLOGY: linear (ii) MOLECULE TYPE: genomic DNA (x) PUBLICATION INFORMATION:
                (A) AUTHORS: Kimura, A.
                             Sasazuki, T.
                (B) TITLE: Eleventh International Histocompatibility
                        Workshop Reference Protocol for the HLA-DNA-Typing
                        Technique
                (C) JOURNAL: HLA 1991
                (D) VOLUME: 1
                (F) PAGES: 397-419
                (G) DATE: 1992
                (K) RELEVANT RESIDUES IN SEQ ID NO: 89: 1 to 18

(xi) SEQUENCE DESCRIPTION: SEQ ID NO: 89:

ACCGCGGCCC GCTTCTGC                                                                                    18

(2) INFORMATION FOR SEQ ID NO:90:

(i) SEQUENCE CHARACTERISTICS:
                (A) LENGTH: 18 nucleotides
                (B) TYPE: nucleic acid
                (C) STRANDEDNESS: single
                (D) TOPOLOGY: linear (ii) MOLECULE TYPE: genomic DNA (x) PUBLICATION INFORMATION:
                (A) AUTHORS: Kimura, A.
                             Sasazuki, T.
                (B) TITLE: Eleventh International Histocompatibility
                        Workshop Reference Protocol for the HLA-DNA-Typing
                        Technique
                (C) JOURNAL: HLA 1991

(D) VOLUME: 1
(F) PAGES: 397-419
(G) DATE: 1992
(K) RELEVANT RESIDUES IN SEQ ID NO: 90: 1 to 18

(xi) SEQUENCE DESCRIPTION: SEQ ID NO: 90:

GCAGAGGCGG GCCGAGGT                                                18

(2) INFORMATION FOR SEQ ID NO:91:

(i) SEQUENCE CHARACTERISTICS:
      (A) LENGTH: 18 nucleotides
      (B) TYPE: nucleic acid
      (C) STRANDEDNESS: single
      (D) TOPOLOGY: linear (ii) MOLECULE TYPE: genomic DNA (x) PUBLICATION INFORMATION:
      (A) AUTHORS: Kimura, A.
                Sasazuki, T.
      (B) TITLE: Eleventh International Histocompatibility
           Workshop Reference Protocol for the HLA-DNA-Typing
           Technique
      (C) JOURNAL: HLA 1991
      (D) VOLUME: 1
      (F) PAGES: 397-419
      (G) DATE: 1992
      (K) RELEVANT RESIDUES IN SEQ ID NO: 91: 1 to 18

(xi) SEQUENCE DESCRIPTION: SEQ ID NO: 91:

ACATCCTGGA AGACGAGC                                                18

(2) INFORMATION FOR SEQ ID NO:92:

(i) SEQUENCE CHARACTERISTICS:
      (A) LENGTH: 18 nucleotides
      (B) TYPE: nucleic acid
      (C) STRANDEDNESS: single
      (D) TOPOLOGY: linear (ii) MOLECULE TYPE: genomic DNA (x) PUBLICATION INFORMATION:
      (A) AUTHORS: Kimura, A.
                Sasazuki, T.
      (B) TITLE: Eleventh International Histocompatibility
           Workshop Reference Protocol for the HLA-DNA-Typing
           Technique
      (C) JOURNAL: HLA 1991
      (D) VOLUME: 1
      (F) PAGES: 397-419
      (G) DATE: 1992
      (K) RELEVANT RESIDUES IN SEQ ID NO: 92: 1 to 18

(xi) SEQUENCE DESCRIPTION: SEQ ID NO: 92:

ACTTCCTGGA AGACGAGC                                                18

(2) INFORMATION FOR SEQ ID NO:93:

(i) SEQUENCE CHARACTERISTICS:
      (A) LENGTH: 18 nucleotides
      (B) TYPE: nucleic acid
      (C) STRANDEDNESS: single
      (D) TOPOLOGY: linear (ii) MOLECULE TYPE: genomic DNA (x) PUBLICATION INFORMATION:
      (A) AUTHORS: Kimura, A.
                Sasazuki, T.
      (B) TITLE: Eleventh International Histocompatibility
           Workshop Reference Protocol for the HLA-DNA-Typing
           Technique (C) JOURNAL: HLA 1991
(D) VOLUME: 1
(F) PAGES: 397-419
(G) DATE: 1992
(K) RELEVANT RESIDUES IN SEQ ID NO: 93: 1 to 18

(xi) SEQUENCE DESCRIPTION: SEQ ID NO: 93:

AGCGGAGGCG GGCCGAGG 18

(2) INFORMATION FOR SEQ ID NO:94:

(i) SEQUENCE CHARACTERISTICS:
(A) LENGTH: 18 nucleotides
(B) TYPE: nucleic acid
(C) STRANDEDNESS: single
(D) TOPOLOGY: linear (ii) MOLECULE TYPE: genomic DNA (x) PUBLICATION INFORMATION:
(A) AUTHORS: Kimura, A.
Sasazuki, T.
(B) TITLE: Eleventh International Histocompatibility Workshop Reference Protocol for the HLA-DNA-Typing Technique
(C) JOURNAL: HLA 1991
(D) VOLUME: 1
(F) PAGES: 397-419
(G) DATE: 1992
(K) RELEVANT RESIDUES IN SEQ ID NO: 94: 1 to 18

(xi) SEQUENCE DESCRIPTION: SEQ ID NO: 94:

GGACATCCTG GAAGACAG 18

(2) INFORMATION FOR SEQ ID NO:95:

(i) SEQUENCE CHARACTERISTICS:
(A) LENGTH: 18 nucleotides
(B) TYPE: nucleic acid
(C) STRANDEDNESS: single
(D) TOPOLOGY: linear (ii) MOLECULE TYPE: genomic DNA (x) PUBLICATION INFORMATION:
(A) AUTHORS: Kimura, A.
Sasazuki, T.
(B) TITLE: Eleventh International Histocompatibility Workshop Reference Protocol for the HLA-DNA-Typing Technique
(C) JOURNAL: HLA 1991
(D) VOLUME: 1
(F) PAGES: 397-419
(G) DATE: 1992
(K) RELEVANT RESIDUES IN SEQ ID NO: 95: 1 to 18

(xi) SEQUENCE DESCRIPTION: SEQ ID NO: 95:

GACATCCTGG AGCAGGCG 18

(2) INFORMATION FOR SEQ ID NO:96:

(i) SEQUENCE CHARACTERISTICS:
(A) LENGTH: 18 nucleotides
(B) TYPE: nucleic acid
(C) STRANDEDNESS: single
(D) TOPOLOGY: linear (ii) MOLECULE TYPE: genomic DNA (x) PUBLICATION INFORMATION:
(A) AUTHORS: Kimura, A.
Sasazuki, T.
(B) TITLE: Eleventh International Histocompatibility Workshop Reference Protocol for the HLA-DNA-Typing Technique
            (C) JOURNAL: HLA 1991
            (D) VOLUME: 1
            (F) PAGES: 397-419
            (G) DATE: 1992
            (K) RELEVANT RESIDUES IN SEQ ID NO: 96: 1 to 18

(xi) SEQUENCE DESCRIPTION: SEQ ID NO: 96:

ACCTCGGCCC GCCTCTGC 18

(2) INFORMATION FOR SEQ ID NO:97:

(i) SEQUENCE CHARACTERISTICS:
            (A) LENGTH: 18 nucleotides
            (B) TYPE: nucleic acid
            (C) STRANDEDNESS: single
            (D) TOPOLOGY: linear (ii) MOLECULE TYPE: genomic DNA (x) PUBLICATION INFORMATION:
            (A) AUTHORS: Kimura, A.
                    Sasazuki, T.
            (B) TITLE: Eleventh International Histocompatibility
                    Workshop Reference Protocol for the HLA-DNA-Typing
                    Technique
            (C) JOURNAL: HLA 1991
            (D) VOLUME: 1
            (F) PAGES: 397-419
            (G) DATE: 1992
            (K) RELEVANT RESIDUES IN SEQ ID NO: 97: 1 to 18

(xi) SEQUENCE DESCRIPTION: SEQ ID NO: 97:

CCAAGAGGAG TCCGTGCG 18

(2) INFORMATION FOR SEQ ID NO:98:

(i) SEQUENCE CHARACTERISTICS:
            (A) LENGTH: 18 nucleotides
            (B) TYPE: nucleic acid
            (C) STRANDEDNESS: single
            (D) TOPOLOGY: linear (ii) MOLECULE TYPE: genomic DNA (x) PUBLICATION INFORMATION:
            (A) AUTHORS: Kimura, A.
                    Sasazuki, T.
            (B) TITLE: Eleventh International Histocompatibility
                    Workshop Reference Protocol for the HLA-DNA-Typing
                    Technique
            (C) JOURNAL: HLA 1991
            (D) VOLUME: 1
            (F) PAGES: 397-419
            (G) DATE: 1992
            (K) RELEVANT RESIDUES IN SEQ ID NO: 98: 1 to 18

(xi) SEQUENCE DESCRIPTION: SEQ ID NO: 98:

AACCAGGAGG AGTCCGTG 18

(2) INFORMATION FOR SEQ ID NO:99:

(i) SEQUENCE CHARACTERISTICS:
            (A) LENGTH: 18 nucleotides
            (B) TYPE: nucleic acid
            (C) STRANDEDNESS: single
            (D) TOPOLOGY: linear (ii) MOLECULE TYPE: genomic DNA (x) PUBLICATION INFORMATION:
            (A) AUTHORS: Kimura, A.
                    Sasazuki, T.
            (B) TITLE: Eleventh International Histocompatibility Workshop Reference Protocol for the HLA-DNA-Typing
Technique
( C ) JOURNAL: HLA 1991
( D ) VOLUME: 1
( F ) PAGES: 397-419
( G ) DATE: 1992
( K ) RELEVANT RESIDUES IN SEQ ID NO: 99: 1 to 18

( x i ) SEQUENCE DESCRIPTION: SEQ ID NO: 99:

ACCAGGAGGA GAACGTGC 18

( 2 ) INFORMATION FOR SEQ ID NO:100:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( x ) PUBLICATION INFORMATION:
        ( A ) AUTHORS: Kimura, A.
            Sasazuki, T.
        ( B ) TITLE: Eleventh International Histocompatibility
            Workshop Reference Protocol for the HLA-DNA-Typing
            Technique
        ( C ) JOURNAL: HLA 1991
        ( D ) VOLUME: 1
        ( F ) PAGES: 397-419
        ( G ) DATE: 1992
        ( K ) RELEVANT RESIDUES IN SEQ ID NO: 100: 1 to 18

( x i ) SEQUENCE DESCRIPTION: SEQ ID NO: 100:

ATCACCAAGA GGAGTACG 18

( 2 ) INFORMATION FOR SEQ ID NO:101:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( x ) PUBLICATION INFORMATION:
        ( A ) AUTHORS: Kimura, A.
            Sasazuki, T.
        ( B ) TITLE: Eleventh International Histocompatibility
            Workshop Reference Protocol for the HLA-DNA-Typing
            Technique
        ( C ) JOURNAL: HLA 1991
        ( D ) VOLUME: 1
        ( F ) PAGES: 397-419
        ( G ) DATE: 1992
        ( K ) RELEVANT RESIDUES IN SEQ ID NO: 101: 1 to 18

( x i ) SEQUENCE DESCRIPTION: SEQ ID NO: 101:

CCAGGAGGAG CTCCTGCG 18

( 2 ) INFORMATION FOR SEQ ID NO:102:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: genomic DNA ( x ) PUBLICATION INFORMATION:
        ( A ) AUTHORS: Kimura, A.
            Sasazuki, T.

(B) TITLE: Eleventh International Histocompatibility
Workshop Reference Protocol for the HLA-DNA-Typing
Technique
(C) JOURNAL: HLA 1991
(D) VOLUME: 1
(F) PAGES: 397-419
(G) DATE: 1992
(K) RELEVANT RESIDUES IN SEQ ID NO: 102: 1 to 18

(x i) SEQUENCE DESCRIPTION: SEQ ID NO: 102:

CCAAGAGGAA TACGTGCG                                           18

(2) INFORMATION FOR SEQ ID NO:103:

(i) SEQUENCE CHARACTERISTICS:
(A) LENGTH: 18 nucleotides
(B) TYPE: nucleic acid
(C) STRANDEDNESS: single
(D) TOPOLOGY: linear (ii) MOLECULE TYPE: genomic DNA (x) PUBLICATION INFORMATION:
(A) AUTHORS: Kimura, A.
Sasazuki, T.
(B) TITLE: Eleventh International Histocompatibility
Workshop Reference Protocol for the HLA-DNA-Typing
Technique
(C) JOURNAL: HLA 1991
(D) VOLUME: 1
(F) PAGES: 397-419
(G) DATE: 1992
(K) RELEVANT RESIDUES IN SEQ ID NO: 103: 1 to 18

(x i) SEQUENCE DESCRIPTION: SEQ ID NO: 103:

AACCAAGAGG AGAACGTG                                           18

(2) INFORMATION FOR SEQ ID NO:104:

(i) SEQUENCE CHARACTERISTICS:
(A) LENGTH: 18 nucleotides
(B) TYPE: nucleic acid
(C) STRANDEDNESS: single
(D) TOPOLOGY: linear (ii) MOLECULE TYPE: genomic DNA (x) PUBLICATION INFORMATION:
(A) AUTHORS: Kimura, A.
Sasazuki, T.
(B) TITLE: Eleventh International Histocompatibility
Workshop Reference Protocol for the HLA-DNA-Typing
Technique
(C) JOURNAL: HLA 1991
(D) VOLUME: 1
(F) PAGES: 397-419
(G) DATE: 1992
(K) RELEVANT RESIDUES IN SEQ ID NO: 104: 1 to 18

(x i) SEQUENCE DESCRIPTION: SEQ ID NO: 104:

GCGCGTACTC CTCTTGGT                                           18

(2) INFORMATION FOR SEQ ID NO:105:

(i) SEQUENCE CHARACTERISTICS:
(A) LENGTH: 18 nucleotides
(B) TYPE: nucleic acid
(C) STRANDEDNESS: single
(D) TOPOLOGY: linear (ii) MOLECULE TYPE: genomic DNA (x) PUBLICATION INFORMATION:
(A) AUTHORS: Kimura, A.

Sasazuki, T.
(B) TITLE: Eleventh International Histocompatibility
Workshop Reference Protocol for the HLA-DNA-Typing
Technique
(C) JOURNAL: HLA 1991
(D) VOLUME: 1
(F) PAGES: 397-419
(G) DATE: 1992
(K) RELEVANT RESIDUES IN SEQ ID NO: 105: 1 to 18

(x i) SEQUENCE DESCRIPTION: SEQ ID NO: 105:

GGAGGACTTG CGCTTCGA 18

(2) INFORMATION FOR SEQ ID NO:106:

(i) SEQUENCE CHARACTERISTICS:
(A) LENGTH: 18 nucleotides
(B) TYPE: nucleic acid
(C) STRANDEDNESS: single
(D) TOPOLOGY: linear (i i) MOLECULE TYPE: genomic DNA (x) PUBLICATION INFORMATION:
(A) AUTHORS: Kimura, A.
Sasazuki, T.
(B) TITLE: Eleventh International Histocompatibility
Workshop Reference Protocol for the HLA-DNA-Typing
Technique
(C) JOURNAL: HLA 1991
(D) VOLUME: 1
(F) PAGES: 397-419
(G) DATE: 1992
(K) RELEVANT RESIDUES IN SEQ ID NO: 106: 1 to 18

(x i) SEQUENCE DESCRIPTION: SEQ ID NO: 106:

CAGGAGGAGT TCCTGCGC 18

(2) INFORMATION FOR SEQ ID NO:107:

(i) SEQUENCE CHARACTERISTICS:
(A) LENGTH: 18 nucleotides
(B) TYPE: nucleic acid
(C) STRANDEDNESS: single
(D) TOPOLOGY: linear (i i) MOLECULE TYPE: genomic DNA (x) PUBLICATION INFORMATION:
(A) AUTHORS: Kimura, A.
Sasazuki, T.
(B) TITLE: Eleventh International Histocompatibility
Workshop Reference Protocol for the HLA-DNA-Typing
Technique
(C) JOURNAL: HLA 1991
(D) VOLUME: 1
(F) PAGES: 397-419
(G) DATE: 1992
(K) RELEVANT RESIDUES IN SEQ ID NO: 107: 1 to 18

(x i) SEQUENCE DESCRIPTION: SEQ ID NO: 107:

AGGAGGAGTA CGCGCGCT 18

(2) INFORMATION FOR SEQ ID NO:108:

(i) SEQUENCE CHARACTERISTICS:
(A) LENGTH: 18 nucleotides
(B) TYPE: nucleic acid
(C) STRANDEDNESS: single
(D) TOPOLOGY: linear (i i) MOLECULE TYPE: genomic DNA (x) PUBLICATION INFORMATION:

(A) AUTHORS: Kimura, A.
    Sasazuki, T.
(B) TITLE: Eleventh International Histocompatibility
    Workshop Reference Protocol for the HLA-DNA-Typing
    Technique
(C) JOURNAL: HLA 1991
(D) VOLUME: 1
(F) PAGES: 397-419
(G) DATE: 1992
(K) RELEVANT RESIDUES IN SEQ ID NO: 108: 1 to 18

(xi) SEQUENCE DESCRIPTION: SEQ ID NO: 108:

CAGGAGGAGT TCGTGCGC    18

(2) INFORMATION FOR SEQ ID NO:109:

(i) SEQUENCE CHARACTERISTICS:
    (A) LENGTH: 18 nucleotides
    (B) TYPE: nucleic acid
    (C) STRANDEDNESS: single
    (D) TOPOLOGY: linear (ii) MOLECULE TYPE: genomic DNA (x) PUBLICATION INFORMATION:
    (A) AUTHORS: Kimura, A.
        Sasazuki, T.
    (B) TITLE: Eleventh International Histocompatibility
        Workshop Reference Protocol for the HLA-DNA-Typing
        Technique
    (C) JOURNAL: HLA 1991
    (D) VOLUME: 1
    (F) PAGES: 397-419
    (G) DATE: 1992
    (K) RELEVANT RESIDUES IN SEQ ID NO: 109: 1 to 18

(xi) SEQUENCE DESCRIPTION: SEQ ID NO: 109:

GCGCACGTAC TCCTCTTG    18

(2) INFORMATION FOR SEQ ID NO:110:

(i) SEQUENCE CHARACTERISTICS:
    (A) LENGTH: 18 nucleotides
    (B) TYPE: nucleic acid
    (C) STRANDEDNESS: single
    (D) TOPOLOGY: linear (ii) MOLECULE TYPE: genomic DNA (x) PUBLICATION INFORMATION:
    (A) AUTHORS: Kimura, A.
        Sasazuki, T.
    (B) TITLE: Eleventh International Histocompatibility
        Workshop Reference Protocol for the HLA-DNA-Typing
        Technique
    (C) JOURNAL: HLA 1991
    (D) VOLUME: 1
    (F) PAGES: 397-419
    (G) DATE: 1992
    (K) RELEVANT RESIDUES IN SEQ ID NO: 110: 1 to 18

(xi) SEQUENCE DESCRIPTION: SEQ ID NO: 110:

TAACCAAGAG GAGTCCGT    18

(2) INFORMATION FOR SEQ ID NO:111:

(i) SEQUENCE CHARACTERISTICS:
    (A) LENGTH: 18 nucleotides
    (B) TYPE: nucleic acid
    (C) STRANDEDNESS: single
    (D) TOPOLOGY: linear (ii) MOLECULE TYPE: genomic DNA ( x ) PUBLICATION INFORMATION:
  ( A ) AUTHORS: Kimura, A.
          Sasazuki, T.
  ( B ) TITLE: Eleventh International Histocompatibility
          Workshop Reference Protocol for the HLA-DNA-Typing
          Technique
  ( C ) JOURNAL: HLA 1991
  ( D ) VOLUME: 1
  ( F ) PAGES: 397-419
  ( G ) DATE: 1992
  ( K ) RELEVANT RESIDUES IN SEQ ID NO: 111: 1 to 18

( x i ) SEQUENCE DESCRIPTION: SEQ ID NO: 111:

ATCACCAAGA GGAGTCCG          18

( 2 ) INFORMATION FOR SEQ ID NO:112:

( i ) SEQUENCE CHARACTERISTICS:
      ( A ) LENGTH: 18 nucleotides
      ( B ) TYPE: nucleic acid
      ( C ) STRANDEDNESS: single
      ( D ) TOPOLOGY: linear ( i i ) MOLECULE TYPE: genomic DNA ( x ) PUBLICATION INFORMATION:
      ( A ) AUTHORS: Kimura, A.
              Sasazuki, T.
      ( B ) TITLE: Eleventh International Histocompatibility
              Workshop Reference Protocol for the HLA-DNA-Typing
              Technique
      ( C ) JOURNAL: HLA 1991
      ( D ) VOLUME: 1
      ( F ) PAGES: 397-419
      ( G ) DATE: 1992
      ( K ) RELEVANT RESIDUES IN SEQ ID NO: 112: 1 to 18

( x i ) SEQUENCE DESCRIPTION: SEQ ID NO: 112:

AACGGGAGGA GAACCTGC          18

POLYMERS OF OLIGONUCLEOTIDE PROBES AS THE BOUND LIGANDS FOR USE IN REVERSE DOT BLOTS

This is a continuation of application Ser. No. 07/786,228 filed on Oct. 31, 1991 abandoned.

ACKNOWLEDGMENT

The present invention was developed in part with government support under grant number AI23963 awarded by the National Institutes of Health. The government has certain rights in this invention.

FIELD OF THE INVENTION

The present invention relates generally to methods and materials for facilitating the detection of specific nucleotide sequences. More particularly the present invention is directed to the use of enzymatic amplification techniques to generate polymers of oligonucleotide probes for use in reverse dot blot procedures which may be used for detecting the presence of disease associated genes and particularly for HLA molecular typing.

BACKGROUND OF THE INVENTION

The human major histocompatibility complex (HLA) encompasses three classes of molecules that control nearly all aspects of human immune response including immunological rejection of organ transplants. The HLA genes are found on the short arm of chromosome 6 and encode a set of highly polymorphic integral membrane proteins that bind antigen peptide fragments. The expressed class II molecules, DP, DQ, and DR, each have defined sub-regions that are also highly polymorphic. In general, HLA typing is useful in tissue typing for transplantation and analysis of genetic susceptibility to certain autoimmune diseases. See Duquesnoy, J. R., et al., *CRC Critical Reviews in Immunology* 8:103 (1988), the disclosure of which is incorporated herein by reference.

The exponential expansion of tissue transplantations being performed has resulted in increased requests for donor-recipient HLA matching by HLA typing. Id. Additionally, HLA typing is also being performed to ascertain the risk of developing certain HLA-linked autoimmune diseases. See Bertrans, J., et al., *Histocompatibility Testing* Heidelberg: Springer-Verlag pp. 348–356 (1984); Todd, J. A., et al., *Nature* 329:559 (1987); and Morel, P., et al., *P.N.A.S. USA* 85:8111 (1988), the disclosures of which are incorporated herein by reference. In the case of autoimmune disease assessment, HLA class II typing appears to be more important than HLA class I typing. Trucco, M., et al., *Critical Reviews in Immunology* 9:201 (1989), the disclosure of which is incorporated herein by reference. For these purposes, however, the characterization of the alleles of HLA class II molecules by serological typing clearly has significant limitations: there are limited amounts of the most used anti-class II antisera; there are difficulties in obtaining reproducible tests since sera from two donors, or even the same donor at different times, do not have exactly the same specificity, and many allelic variations, such as DP, are not recognized by the alloantisera; and successful class II HLA typing requires a well purified population of B lymphocytes that can only be obtained from a relatively large quantity of blood. The main advantage of serological typing as opposed to typing at the molecular level is that very good, although incomplete, results are possible in less than 24 hours. At the present time, molecular approaches have entailed relatively complex technical procedures and thus have not been able to match this time schedule.

HLA typing at the molecular level, although extremely more precise and more complete than the serological typing, is limited in its applications by the complexity of either performing a restriction fragment length polymorphism (RFLP) analysis, or using oligonucleotides as probes. RFLP analysis, as is well known in the art, uses for each DNA probe a particular set of restriction enzymes to digest the genomic DNA of the donor that is to be typed, and is not easily practiced in all laboratories. In some laboratories, for instance, the use of radioactivity may pose a problem, while in others, it may not be easy to correctly perform Southern blots, especially if many tests have to be performed in a short amount of time. Also, many laboratories do not have the expertise or equipment to properly expand the DNAs used as probes and to label them appropriately.

Recently another technology, polymerase chain reaction ("PCR"), has been used to detect polymorphic restriction sites and nucleic acid sequences and has obviated many of the aforementioned limiting aspects of Southern blots. PCR methods are described in U.S. Pat. Nos. 4,683,195; 4,683, 202; and 4,889,818 (Taq DNA Polymerase) and in Saiki, R. K. et al., *Science* 230: 1350 (1985), the disclosures of which are incorporated herein by reference. Briefly, PCR is a process for amplifying any target nucleic acid sequence contained in a nucleic acid. To amplify a given nucleic acid sequence, separate complementary (denatured) strands of the nucleic acid sequence are treated with a molar excess of two oppositely oriented converging oligonucleotide primers which flank the target sequence. The primers anneal to the separate strands such that when the primers are extended with one or both of reverse transcriptase and a DNA polymerase, repeated extensions of the primers yield copies of the target nucleic acid sequence that occur between the two primers. At the end of each extension cycle the complementary primer extension products are denatured and serve as templates for the next cycle of primer annealing and primer extension, thereby essentially doubling the amount of the DNA sequence over that synthesized in the previous cycle. The result is an exponential amplification of target sequence, approximately $2^n$, where n is the number of cycles. Through PCR amplification it is possible to detect small amounts of DNA in samples where it would otherwise be undetectable with standard nucleic acid hybridization methods as described above.

One of the methods often used to detect the in presence or absence of specific nucleotide sequences is DNA, and used widely in current HLA typing procedures, the dot blot technique as described by Southern, E. M., *J. Mol. Bio.* 98:503 (1975). By this technique, denatured (single-stranded) target DNA is anchored to a membrane and the membrane is subsequently treated with a solution containing a short, labeled and denatured specific DNA probe under conditions such that a segment of the bound target DNA and the specific probe hybridize. The non-hybridized probes are then washed away and the retention of the specific probe is determined by several methods well known in the art, all of which require prior attachment of a reporter moiety or label to the probe. The most commonly used method to trace the probe involves the autoradiography of $^{32}$P incorporated into the probe. Since its original description, the dot blot has been modified by using PCR to amplify the particular sequence to be probed. With this improvement the dot blot technique is useful to determine the presence of a specific nucleotide sequence or the presence of even a single nucleotide variation in a certain sequence, because the stringency conditions can be tailored to each probe.

Another technique used to detect nucleotide sequences is the so-called reverse dot blot technique. The reverse dot blot technique differs from the conventional dot blot technique in that the ligand anchored to the membrane is the oligonucleotide probe rather than the sample or target DNA whose presence is being tested for. In such a technique a reporter moiety is attached to the sample DNA being tested instead of the specific probe as is the case for conventional dot blots. The reverse dot blot technique has several advantages over conventional dot blot techniques. First, many specific probes can be anchored to a single membrane at different positions and the hybridization can therefore be carried out simultaneously in a single container instead of separate containers for each specific probe. Thus, in a single hybridization reaction, an entire series of sequences can be analyzed simultaneously. An additional advantage of this technique is that a singe preparation of DNA containing the reporter moiety can be used for a large number of specific bound probes, whereas the conventional dot blot technique required each individual probe to be labeled separately. This advantage is particularly important when the results from several probes must be compared. For the individually labeled probes, corrections must be introduced to compensate for differences in the labeling of each probe, whereas the labeled DNA in the reverse dot blot is the same for the interaction with each probe and the results of each specific hybridization can be directly compared.

The specific oligonucleotide probes used to practice the reverse dot blot technique are preferably about 14 to about 20 nucleotides long. There are, however, disadvantages associated with direct attachment of probes of this size to membranes. First, the overall attachment process is not efficient. Second, the probes are attached to the membrane by formation of a chemical bond to part of the specific sequence which thereby reduces the specificity or ability of the probe to discriminate at the level of a single DNA base-pair mismatch. The art has evolved to overcome these problems by enzymatic alteration of probes to add a relatively large number of thymidine nucleotides at the 3' end of probes to form a deoxyribothymidine homopolymer tail. This procedure, also known as poly dT tailing, is described by Saiki, R. K., et al., *P.N.A.S.* (USA) 86:8230 (1989), the disclosure of which is incorporated herein by reference. The increase in the size of the probe due to the addition of the poly dT tail has the effect of increasing the binding efficiency of probes to membranes and in many instances the chemical bonds with the membrane will occur within the poly dT tail rather than the specific binding sequence, thereby maintaining probe specificity.

PCR protocols have been particularly useful to detect genetic variations in the HLA region. Using PCR methods and the conventional dot blot it has been possible, for example, to molecularly type hundreds of samples for determining whether or not variations in the short segment centered on codon 57 of the second exon of the HLA-DQB1 gene were reliable markers for insulin-dependent diabetes mellitus susceptibility as described by Morel, P., et al., *P.N.A.S.* (USA) 85:8111 (1988); Bao, M. Z., et al., *Lancet* 2:297 (1989); Carcassi, C., et al., *Human Immunology* 31:159 (1991); and Dorman, J., et al., *P.N.A.S.* (USA) 87:7370 (1990), the disclosures of which are incorporated herein by reference. Despite the fact that high quality results using this approach were generated, it is clear that a complete class II molecular typing would be much more demanding than just testing the polymorphism at only one segment of a single gene. For example, the reference protocols for the XI International Histocompatibility Workshop (1990), the disclosure of which is incorporated herein by reference lists 140 necessary oligonucleotides for a complete class II typing. Each of the oligonucleotides must be used as independently labeled hybridization probes and must be stringently washed at specific temperatures. Clearly, the labeling and manipulation of all 140 of the oligonucleotides and filters would be extremely impractical for routine tests. Additionally, there are extremely high costs for the necessary radioactive reagents, PCR reagents (e.g., Taq DNA polymerase), nitrocellulose filters, and specialized personnel.

The use of RFLP analysis on specifically PCR amplified DNA for HLA typing is described by Trucco, G., et al., *Diabetes* 38:1617 (1989) and Rudert, W. A., et al., *Pharmacy Times*, October 1989 p. 38, the disclosures of which are incorporated herein by reference. Although this approach is advantageous since it is more rapid than the aforementioned methods and it can be performed without either radioactive materials or dot blot procedures, it is still too complex to be carried out by many laboratories.

Erlich, H. A., et al., in *PCR Protocols A Guide To Methods And Applications* Academic Press, Innis, M. A., et al., (Eds.) p. 261 (1990), the disclosure of which is incorporated herein by reference, detail detection of specific HLA alleles in a PCR- amplified sample by dot blot hybridization with labeled oligonucleotide probes as well as a reverse dot blot procedure whereby the oligonucleotide probe is immobilized on a membrane and hybridized to a labeled PCR target DNA product. As reported by Saiki, R. K., et al., *Nature (London)* 324:163 (1986), the disclosure of which is incorporated herein by reference, PCR was used to enzymatically amplify β-globin and HLA-DQα DNA, and the resulting amplification products were probed with allele-specific oligonucleotides to detect allelic variations using the conventional dot blot procedure. See also, Saiki, R. K., et al., *Proc. Natl. Acad. Sci. USA* 86:6230 (1989) (reverse dot blot with poly dT tailing), the disclosure of which is incorporated herein by reference.

The present invention provides an advancement of the reverse dot blot procedure by taking advantage of various aspects of enzymatic amplification procedures.

SUMMARY OF THE INVENTION

Accordingly, it is a primary object of the present invention to provide a more efficient method for detecting specific nucleotide sequences with immobilized sequence-specific oligonucleotide probes.

Another object of the present invention is to provide a method for detecting specific nucleotide sequences with immobilized sequence—specific oligonucleotide probes which allows the probes to retain more of the probe's specific hybridization properties than with conventional reverse dot blot procedures.

Yet another object of the present invention is to synthesize polymers of oligonucleotide probes for use as the bound ligand in reverse dot blots.

Still another object of the present invention is to synthesize long polymers of oligonucleotide monomers using enzymatic amplification procedures for use as the bound ligand in reverse dot blots.

Still another object of the present invention is to provide a permanent source of long polymers of oligonucleotides monomers by cloning the polymers in a suitable host and excising the polymers when needed.

Another object of the present invention is to provide a reverse dot blot procedure whereby both strands of test DNA may hybridize to bound oligonucleotide probes.

Still another object is to provide a reverse dot blot procedure without use of radioactive labels.

Yet another object is to provide a method of complete HLA typing that is precise and fast which uses a very limited amount of blood or other type of tissue.

These and other objects of the present invention are achieved by one or more of the following embodiments.

In one aspect, the invention features a method of detecting the presence or absence of nucleic acid sequences, comprising:

binding to a substrate polymers of selected oligonucleotide probes which are complementary to a region in a nucleic acid sequence which is to be detected;

contacting said substrate to which the probe polymers are bound with an amplified test DNA sample containing unknown oligonucleotide sequences, wherein a reporter moiety has been incorporated, such that complementary nucleotide sequences anneal;

washing the substrate to remove unannealed amplified test DNA from the substrate; and detecting the presence or absence of reporter moieties retained by the oligonucleotide probes on the substrate.

In preferred embodiments of the invention the polymers of selected oligonucleotide probes are synthesized by the steps of:

I. annealing two oligonucleotide primers which are oppositely oriented and share complementarity at their 3' ends and which together either directly or in the form of complementary nucleotides define the sequence of a complete monomeric unit which incorporates the selected oligonucleotide probe sequence as well as a sufficient number of the nucleotides of the adjacent monomeric units such that the primers anneal at their 3' ends and that the 5' ends of the primers are not annealed and function as templates for synthesis of first extension products;

II. treating the primers with a DNA polymerase in the presence of deoxyribonucleotides such that a first extension product of each primer is synthesized which is complementary to each template;

III. separating the complementary first extension products by denaturation to produce single-stranded molecules;

IV. annealing complementary strands of the first extension products at their 3' ends in a staggered arrangement such that the 5' ends are not annealed and function as templates for further extension of the previous extension products;

V. treating the annealed strands using a DNA polymerase and deoxyribonucleotides such that double-stranded extension products are synthesized;

VI. separating the complementary extension products by denaturization; and

VII. repeating steps (d) through (f) using the extension products of step (f) to produce successively longer extension products with each repetition.

In another aspect the invention features a vector derived from pUC18, pUC19, or the bacteriophage M13mp series into which is cloned double-stranded primer extension product.

In other preferred embodiments the invention features bacterial cultures transfected with a vector derived from pUC18, pUC19, or the bacteriophage M13mp series into which is cloned double-stranded primer extension product and methods of producing large quantities of primer extension product polymer comprising:

culturing such bacterium;

recovering the vector containing the polymer; and excising the inserted polymer with restriction endonucleases.

In yet another aspect the invention features a substrate to which selected long polymers of oligonucleotide probes are bound which are complementary to a region in a nucleic acid sequence which is to be determined.

In other embodiments the invention relates to methods for diagnosing the existence of specific nucleic acid sequences suspected of being in a sample and diagnostic kits applicable thereto. A permanent source of long polymers is provided by cloning the polymers in a suitable host which assures reproducibility of diagnostic test results, such as for HLA molecular typing.

DESCRIPTION OF THE DRAWINGS

FIG. 11 shows the primer pairs (SEQ ID NO: 37–SEQ ID NO: 38) and probe sequences required to test all the DRβ sequences. For Primers, SEQ ID NOS: 37–38 are DR1 A, B, respectively; SEQ ID NOS: 39–40 are DR2 A, B, respectively; SEQ ID NOS: 41–42 are DR4 A, B, respectively; SEQ ID NOS: 43–44 are Drw52 associated A, B, respectively; and SEQ ID NOS: 45–46 are DRw52-DRB3 A, B, respectively. For Polymers, SEQ ID NOS: 47–59 are DRB1001–DRB1013, respectively; SEQ ID NOS: 60–62 are DRB8601–DRB8603, respectively; SEQ ID NOS: 63–71 are DRB5701–DRB5709, respectively; SEQ ID NOS: 72–84 are DRB2801–DRB2813, respectively; SEQ ID NOS: 85–96 are DRB7001–DRB7012, respectively; and SEQ ID NOS: 97–112 are DRB3701–DRB3716, respectively.

DETAILED DESCRIPTION OF THE INVENTION

Figure 1:
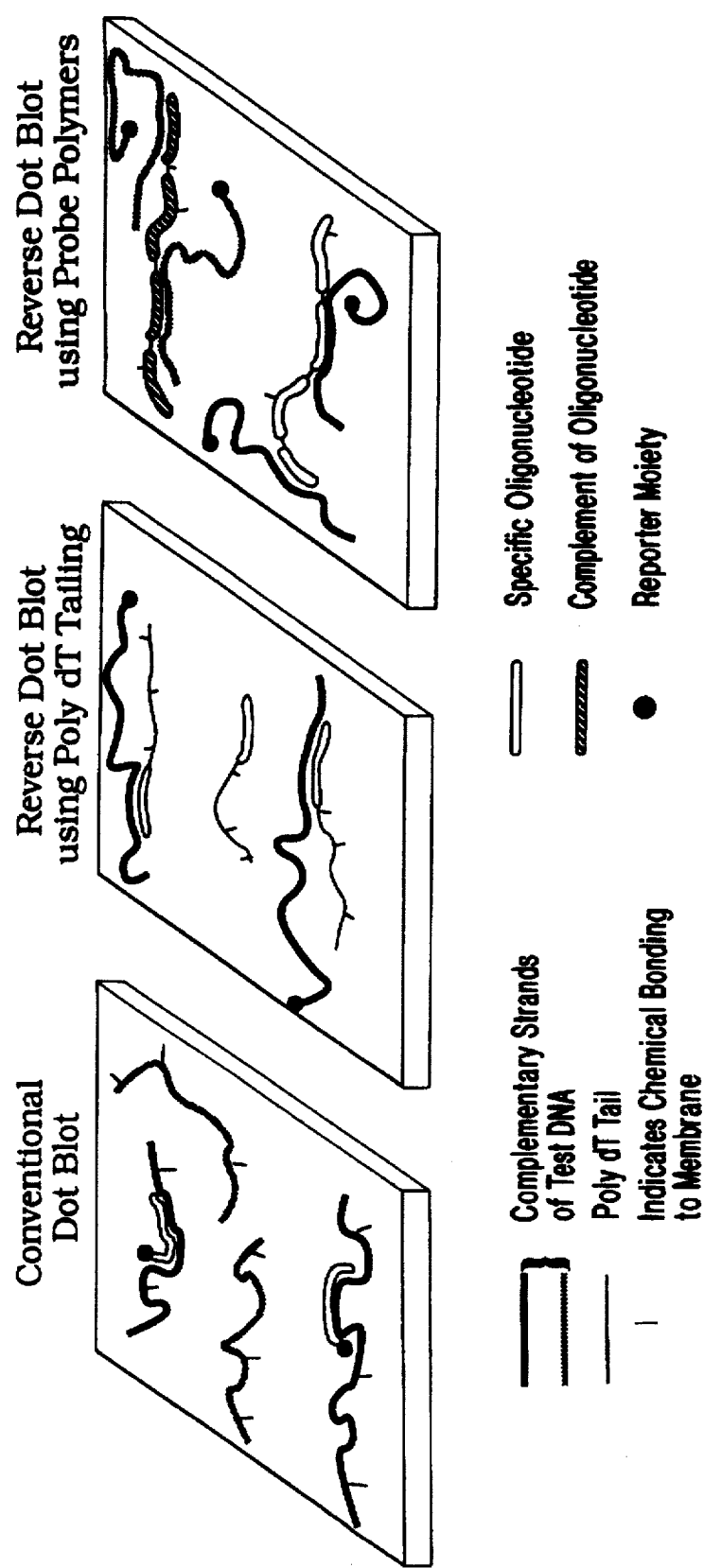
FIG. 1 is a schematic representation of the conventional dot blot technique, the reverse dot blot technique using poly dT tailing, and the reverse dot blot technique using polymers of oligonucleotide probes of the present invention.

As used herein, the term "polymer" refers to single or double-stranded nucleic acid, specifically either RNA or DNA, which contains a nucleotide sequence which is repeated elsewhere in the same molecule at least once. The repeated segments may be arranged tandemly or may be separated by other segments which may vary in length and/or sequence from one location to another. While in theory the repeated elements are exact copies, it is understood that in practice some of the repeated elements may deviate in sequence due to the lack of perfect fidelity of the methods of polymer construction or because of errors such as mutations or deletions that may occur during the propagation of the polymers within vectors in bacteria.

The term "substrate" as used herein refers to rigid or flexible solid support to which nucleic acids can be chemically bound usually by, but not limited to, covalent linkages. The substrate has the additional properties that under different conditions the affinity of the substrate itself for the test DNA and for the reagents of a reporter moiety detection system can be kept minimal. Examples of acceptable types of substrates include, but are not limited to, nylon and nitrocellulose membranes where the covalent linkages are formed as a result of exposure of the substrate and applied DNA to heat or ultraviolet light as is well known and frequently practiced in the art.

These specific requirements could also be satisfied by a substrate which has the additional property that it can be chemically activated to facilitate formation of a covalent bond to the DNA probes in such a way that deactivation of the remaining active sites at a later time would minimize the substrate's affinity for the test DNAs and detection system molecules. An example of such a substrate is diazotizable arylamide cellulose papers as described lose papers as described in Seed, B., *Nucleic Acids Research* 10:1799 (1982), the disclosure of which is incorporated herein by reference.

The term "oligonucleotide" as used herein refers to primers, probes, and oligomer fragments to be detected and is defined as a molecule comprised of two or more deoxyribonucleotides, preferably more than three. Oligonucleotide probes generated by the present invention may be on the order of 2 kilobases.

The present invention provides methods for increasing the binding efficiency and hybridization efficiency of the bound ligand/probe in reverse dot blots. Long polymers, preferably those having about 25 repeats of the specific nucleotide sequence ("monomer") per molecule, such that the polymer length is preferably in the range of between about 200 to 2000 base pairs are prepared to serve as the ligand/probe which are bound to a substrate, for example, a conventional nylon or nitrocellulose membrane, at high efficiency. While the chemical bonds that are formed during binding of the oligonucleotide probe to a substrate necessarily alters some of the probe sequences, only a single bond in one probe sequence is needed to cause sufficient anchoring of the polymeric probe to the substrate. Therefore, more of the probe sequences may be attached to the substrate with each bond or link to the substrate than with the poly dT tailing procedure by virtue of the fact that each bound probe polymer contains so many more copies of the specific nucleotide sequence. The higher probe sequence concentration resulting from the practice of the present invention can result in shorter hybridization times and allow the use of less sensitive detection methods or conditions than with the poly dT tailing method used for conventional reverse dot blots. The test DNA sample that is contacted with the substrate containing the probes is preferably amplified by any suitable amplification procedure.

The presently claimed method further differs from the poly dT tailing method in that both complementary strands of the probe sequence are bound to the membrane. Anchoring of both complementary strands of the probe sequence allows for the possibility that both strands of test DNA will hybridize to the probe rather than only the one strand that is complementary to the poly dT tailed oligonucleotide single-stranded probe in the known method. However, the present invention is not limited to the use of double-stranded polymer probes. When necessary, single-stranded polymers can be prepared with appropriate single-stranded bacteriophage particles using procedures well known in the art.

FIG. 1 is a schematic representation of the conventional dot blot, reverse dot blot using poly dT tailing, and the reverse dot blot using polymers of oligonucleotide probes which is the subject of the present invention.

Synthesis of Polymers of Oligonucleotide Probes

In general, two oligonucleotide primers which are oppositely oriented and which are complementary at their 3' ends are annealed at their 3' ends. The annealed primers, either directly, or by the complementary nucleotides that comprise the eventual extension product, define the sequence of a complete monomer unit which incorporates the particular oligonucleotide probe sequence. Additionally, a sufficient number of the nucleotides of the adjacent monomeric units are incorporated in the primers. The 5' ends of the annealed primers which are not annealed function as templates for synthesis of extension products that are formed when the primers are treated with a DNA polymerase and the four deoxyribonucleoside triphosphates ("dNTPs" or "deoxyribonucleotides"). The first extension products are then denatured by heat or other means or otherwise separated to produce single-stranded DNA molecules. The 3' ends of the single-stranded products may anneal in a staggered arrangement so that the 5' ends do not anneal and thereby function as templates for further extension of the previous extension products. Repetition of the denaturing, extending, and annealing steps causes progressive growth of the polymer.

Figure 2:
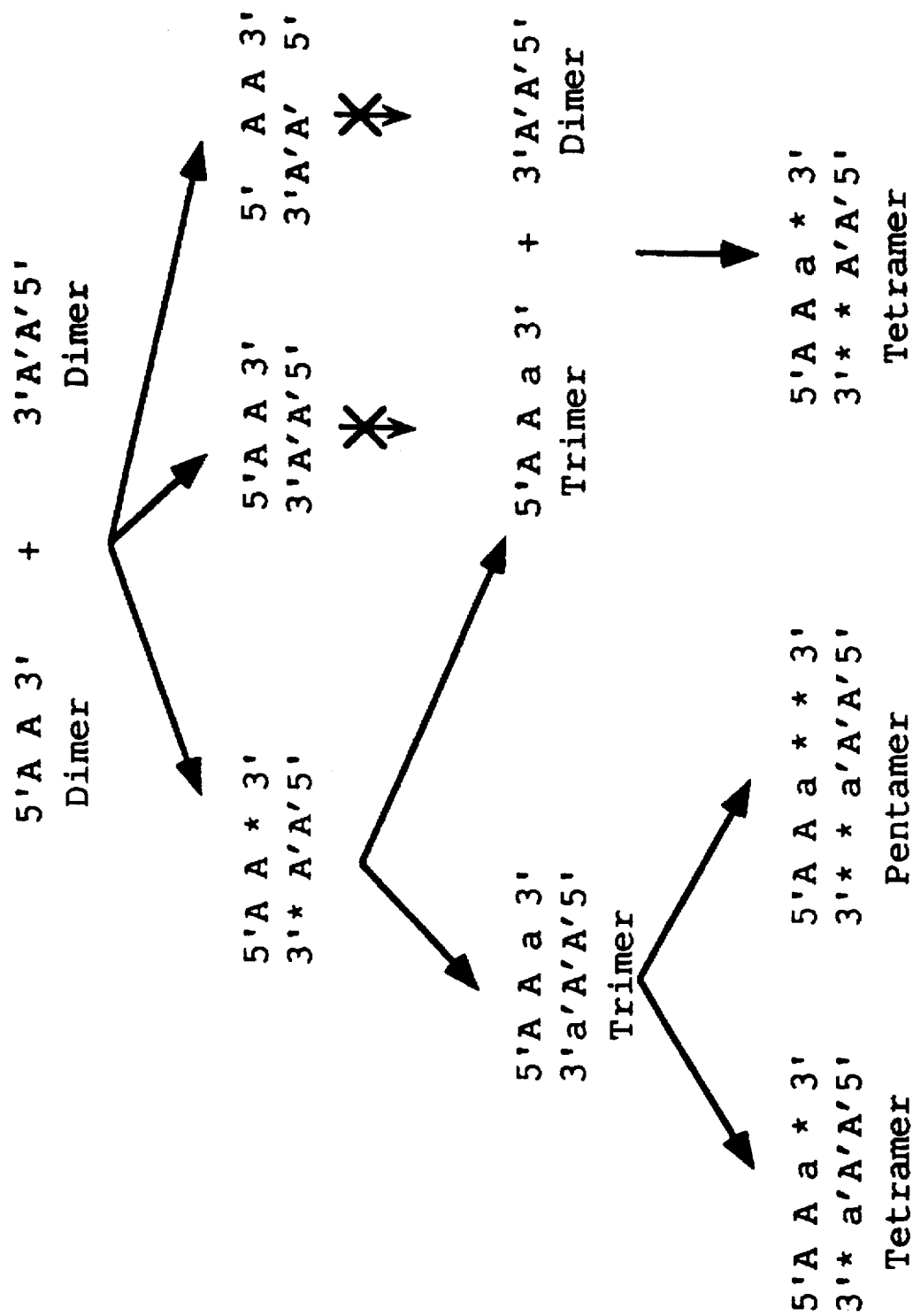
FIG. 2 illustrates synthesis of polymers of oligonucleotide probes by enzymatic amplification with synthetic oligonucleotide dimers.
Figure 3A:
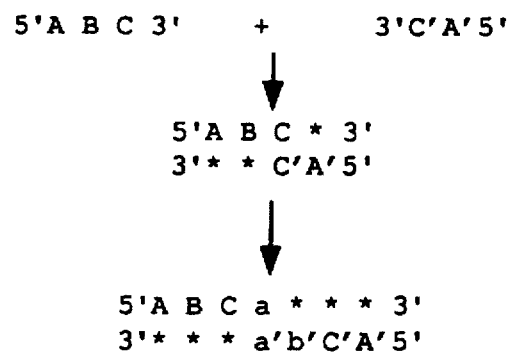
FIGS. 3A and 3B illustrate respectively synthesis of polymers of oligonucleotide probes with shorter primer-template sequences and with primer-template sequences derived from restriction endonuclease digestion of a cloned dimer.
Figure 3B:
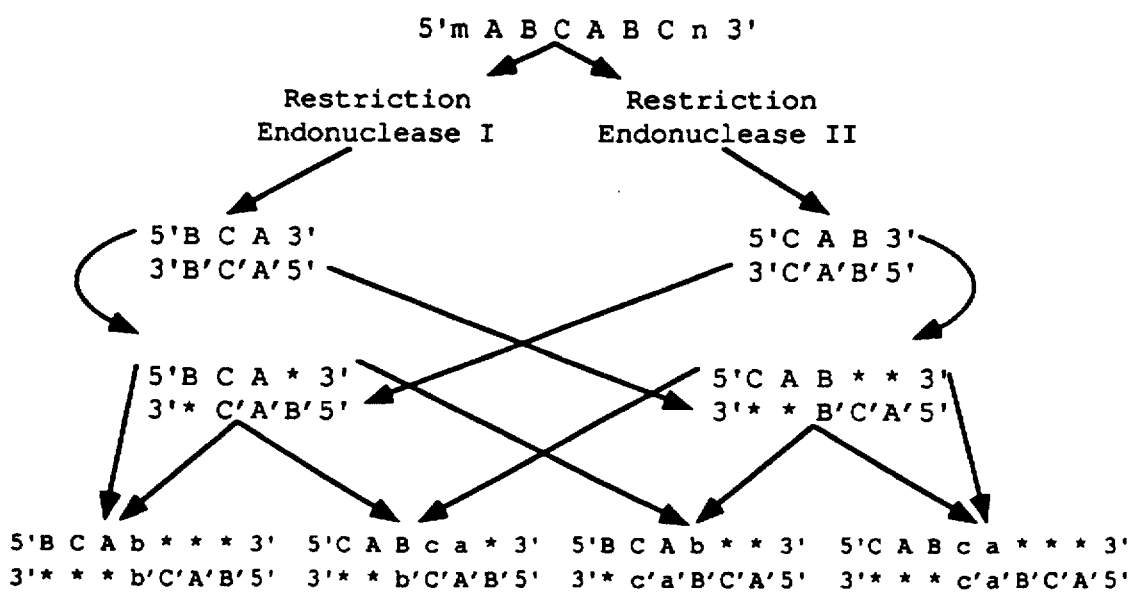

The basic synthesis of polymers of oligonucleotide probes according to the present invention is illustrated in FIG. 2. In FIGS. 2, 3A, and 3B, upper case letters denote any nucleotide sequence, which is usually greater than 12 and less than 50 nucleotides in length. Letters followed by "'" designate the sequence which is complementary to the unmarked letter and also indicates the proper 5'–3' orientation for annealing of the two complementary sequences. Sites available for extension by DNA polymerase or other enzymes are indicated by "*". Lower case letters represent the same nucleotide sequence as the upper case letters, except that these nucleotides have been previously added by DNA polymerase or other enzymes by extension of primers from prior annealings.

As is generally shown in FIG. 2, a pair of complementary dimers of an oligonucleotide sequence is chosen that can anneal in a staggered manner such that the 5' ends of each of the pair protrude and the 3' sequences are annealed. When the complementary dimers are annealed in such a fashion, DNA polymerases or other enzymes or compounds which function to accomplish the synthesis of extension products use the recessed (3') ends as primer sites and the protruding (5') ends as templates for synthesis of a double-stranded trimer when the four deoxyribonucleotides are also added in molar excess. Suitable enzymes for this purpose include, for example, E.coli DNA polymerase I, Klenow fragment of E.coli DNA polymerase I, T4 DNA polymerase, T7 DNA polymerase, thermostable enzymes, and other enzymes which allow for formation of extension products under appropriate conditions. While the pair of dimers can also anneal in two other configurations, i.e., one with flush ends, and the other one with 3' ends protruding and the 5' ends annealed, these other configurations will not allow for DNA polymerases to synthesize extensional DNA. Similarly, the complementary 3' monomeric sequences of a trimer and a dimer can anneal to synthesize a tetramer.

When sufficient quantities of the trimers are present, the complementary trimer sequences are able to anneal in two ways which allow for extension by DNA polymerases or other enzymes to yield either a tetramer or a pentamer. For the synthesis of a tetramer the trimers anneal over a dimeric sequence at their 3' ends and monomeric 5' sequences protrude which act as templates for DNA synthesis. A pentamer is formed when 3' monomeric sequences anneal which allows the 5' dimeric sequences to protrude as templates. A DNA polymerase or other enzyme can then be employed to synthesize double-stranded tetramers and pentamers, respectively.

As can be seen by the foregoing, the annealing of a dimeric sequence such that its 5' end protrudes causes the length of the complementary annealing sequence to increase by one monomer. Similarly, in the case of a multimet of length n, the length of the product is able to increase by as much as n-1 multimet units. As is well known in the art, such a process can be automated using a thermostable enzyme and a temperature cycling procedure. Examples of suitable thermostable enzymes include, Thermus aquaticus DNA polymerase ("Taq Polymerase"), Thermococcus litoralis DNA polymerase, Pyrococcus furiosus DNA polymerase, and other thermostable enzymes which cause formation of extension products under appropriate conditions. In all cases the oligonucleotide primers serve both as primers and templates by their annealing at their respective 3' ends such that their respective 5' ends serve as templates for extension of the primers.

Several variations on this basic synthesis scheme are also possible in accordance with the present invention. According to one of the variations, shown in FIG. 3A, it is not necessary to begin with oligonucleotide primers that both contain the entire dimeric sequence. It is sufficient for the present methods if the double-stranded dimeric molecule can be synthesized in the first rounds of the enzymatic amplification procedure. In practice this variation can be achieved using a thermostable polymerase and a thermocycling procedure. Once a sufficient quantity of the dimeric first extension product has been synthesized the method as described above begins and proceeds automatically during the successive cycles. However, for this variation, the oligonucleotide primers must retain enough of the dimeric sequence to establish the segment of nucleotides which contains the junction between one monomer and the next successive monomer. Thus at least one of the oligonucleotide primers must contain the nucleotide sequence from the 3' end of the monomer sequence (the tail) followed by the more 5' sequence (the head) which would correspond to the beginning of the next successive monomer. In the illustration of FIG. 3A this condition is met by the primer 3'C'A'5' which in the sense of the monomeric sequence represented by 5'ABC3' is comprised of the complementary form of the tail to head junction. Because the eventual product will be multiple repeats of the monomeric sequence, different monomeric sequences can be chosen which begin at any position and continue until the sequence repeats. Thus, the head to tail junction can be positioned at will and need not be determined by the location of the ends of the specific oligonucleotide probe sequence. It should also be noted that in FIG. 3A the length of the nucleotide segment represented by B may range from 0 to greater than 50 nucleotides. When the length of B is only a few nucleotides, slightly different specific sequences may be synthesized using the same common 3'C'A'5' primer. When B is quite large, the monomer 5'ABC3' could be derived from a cloned fragment and the synthetic sequence 3'C'A'5' is derived from the ends of the cloned fragment and establishes the junction between the monomers.

The flexibility of choosing the position of the monomer head and tail can become important to minimize problems with the less specific annealing which is sometimes associated with particular sequences at the 3' ends of primers during amplification procedures. An additional requirement is that the sequence of the 3' end of one primer is complementary to the sequence of the 3' end of the other primers over a sufficient length so that each can properly anneal during the early amplification cycles. Such length needed for annealing is preferably between about at least 12 and 20 or more nucleotides. There is no definite upper limit for the primer sizes which are also dependent on the monomer size. When the intended use of the polymers is for detecting single nuleotide variations, the overall lengths of the primers is preferably between about 20 and 45 nucleotides.

As stated above, in practice this variation can be performed using a thermocycling protocol. During the early cycles sufficient quantities of the dimeric first extension products are synthesized such that the first method as described above can proceed automatically using the first extension products without purification of the intermediate products.

Another variation of the amplification procedure of the present invention, shown in FIG. 3B, can be used when the desired probe sequence has been previously cloned and has within it at least two restriction endonuclease sites. First, a dimer of the desired sequence is constructed by directional cloning techniques as described by Eisenberg, S., et al., *Methods Enzymol.* 182 521 (1990), the disclosure of which is incorporated herein by reference. If desired, one of the two required restriction sites may be introduced during this construction. An appropriate dimer is shown schematically in FIG. 3B where "m" and "n" are flanking vector sequences and restriction endonuclease sites I and II occur at junctions 5'A–B3' and 5'B–C3', respectively. An additional requirement is that the nucleotide sequences between the restriction sites should have sufficient length and properties to anneal in a fashion similar to the head and tail regions in the previously described variations.

Two different, and partially complementary fragments of the cloned dimer can be prepared by digestion with each of the restriction endonucleases and can be then used as the primers and templates during enzymatic amplification. With this synthesis variation as shown in FIG. 3B, once the products of dimer or greater length are synthesized, the reaction can proceed as in the basic synthesis shown in FIG. 2. In this particular variation the starting material is double-stranded and thus, both strands of each of the DNAs are present from the beginning.

The foregoing should not be interpreted to mean that only methods based on the use of DNA polymerases may be used to generate the long polymers used in the practice of the present invention. Any method that may generate long polymers may be used, such as, for example, by directional cloning. A general scheme is described by Eisenberg, S., et al., *Methods Enzymol* 182:521 (1990), the disclosure of which is incorporated herein by reference, whereby a monomer is inserted into a vector which is flanked by two restriction endonuclease sites such as Bgl II and Bam HI which create termini which are compatible for the purpose of annealing and ligating one with the other. When a vector fragment containing the insert cut at the Bam HI site is annealed and ligated to one cut at the Bgl II site, a dimer is created which is flanked by a Bgl II site and a Bam HI site, and contains a Bam HI/Bgl II junction which is not recognized or cut by either enzyme. The process can be successively repeated to create a tetramer from dimers and so forth.

Another method of polymer construction useful for practice of the present invention involves annealing two complementary oligonucleotides to form double-stranded monomers which are simply ligated to form polymers as described by Kadonaga, J. T., et al, *P.N.A.S. USA* 83:5889 (1986), the disclosure of which is incorporated herein by reference. The tendency for this method to produce head to head or tail to tail junctions does not frequently produce long polymers which are stable as vector inserts. However, one possible variation allows the process to have a directional orientation. The oligonucleotides are chosen such that one oligonucleotide's position is shifted relative to the other so that there is a staggered annealing and each oligonucleotide anneals to the opposite ends of two molecules of the complementary oligonucleotide. When many of the adjacent annealed ends are enzymatically ligated, polymers of each DNA strand are formed. Although not essential, the ligation of this method may be performed with thermostable ligases and the efficiency of the method may be improved by using a temperature cycling protocol. Once the ligation step is halted, the extreme ends of the molecules remain staggered, but are converted to blunt ends by the incorporation of nucleotides with DNA polymerase or by cleavage using the 3' exonuclease activity associated with some DNA polymerases depending on whether the 5' or 3' end is protruding, respectively. At this point these polymers may be cloned as in the other aforedescribed methods.

A final method for construction of long polymers would be to chemically synthesize polymers of the two complementary oligonucleotides which are then annealed and cloned in an appropriate vector. However, because these oligonucleotides would also frequently anneal in a staggered manner, the ends would require cutting or filling before cloning as in the previous method.

Once the long polymers have been synthesized by enzymatic or other methods, the reaction or synthesis products may be ligated into a suitable vector such as one from the bacteriophage M13mp series or those phagemids which have been derived from pUC18 or pUC19, examples of which are: pT7/T3α18, pT7/T3α19 (Bethesda Research Laboratories "BRL" Gaithersburg, Md.); pBluescript II SK +/–, pBluescript II KS +/–, pBC SK +/–, pBC KS +/–, and pBS +/–(Stratagene, LaJolla, Calif.). The vector is then transfected into a strain of recombination defective *Escherichia coli* such as XL1-Blue or SURE (Stratagene). See, Sambrook, J., et al., *Molecular Cloning A Laboratory Manual* (2nd Ed.) 1989, pp. 1.74–1.84, the disclosure of which is incorporated herein by reference. Because the products of the aforedescribed syntheses can vary over a considerable size range, it is preferred to select bacterial clones with polymers of the desired number of monomeric repeats. When even longer polymers are desired, the cloned polymeric sequence can be repetitiously duplicated within the vector by directional cloning as was described above. Bacterial stocks may then be prepared from the selected clones to become a permanent source of polymers with uniform size and membrane binding properties. When polymers of a specific oligonucleotide probe are desired for use in a reverse dot blot, they are then prepared by restriction nuclease digestion of large plasmid preparations from the bacteria. For small quantities, the polymers can be amplified from the plasmid by enzymatic amplification methods using T3 and T7 (Stratagene) primers which anneal to the plasmid vector adjacent to the cloning site.

It should be noted that substrates may be prepared whereby the entire vector containing the desired polymers are bound thereto, and the vector may therefore be modified to remove non-essential segments to further increase the proportion of the bound DNA probe sequence.

In the following example DNA polymers of the protein binding region of the HLA DQB1 gene promoter are synthesized.

EXAMPLE 1

Figure 4:
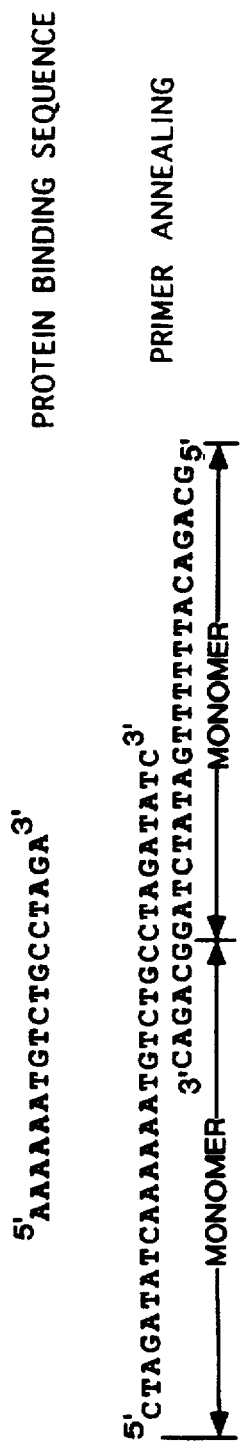
FIG. 4 illustrates the steps and products of enzymatic amplification of a target HLA DQB gene promoter sequence (SEQ ID NO: 2) protein building sequence using two oligonucleotides (bold) (SEQ ID NO: 3 and SEQ ID NO: 4) primer annealing as both primers and templates to produce a polymer ultimately containing many tandemly repeated copies of the sequence (SEQ ID NO: 5–SEQ ID NO: 8) (SEQ ID NO: 5–6—"FIRST EXTENSION"; SEQ ID NO: 7–8—"MULTIMERIC EXTENSION").
Figure 4:
Figure 4:
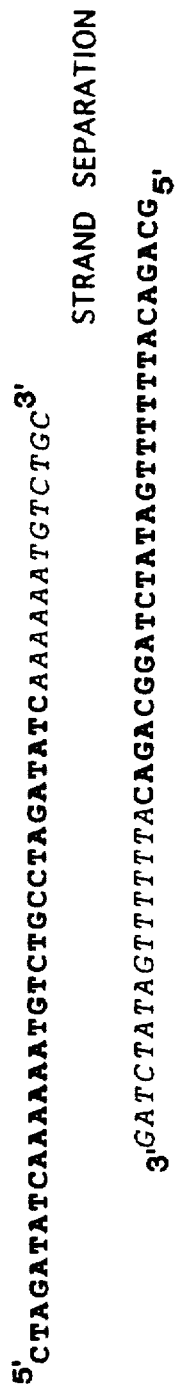
Figure 4:
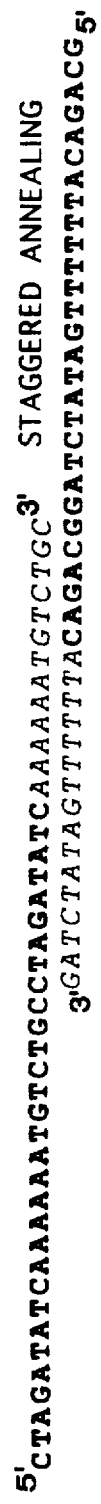
Figure 4:
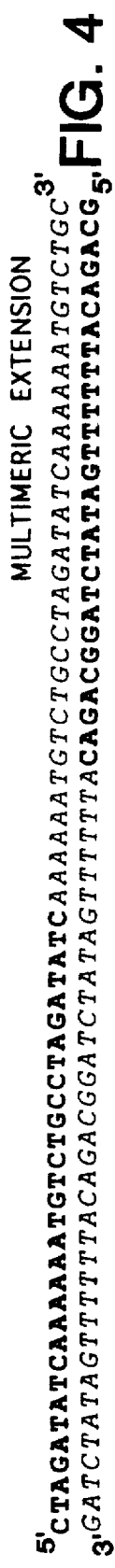

FIG. 4 shows the nucleotide sequences used as primer-templates to create tandem repeats of a methylation protected region of the X-conserved box of the HLA-DQB1 gene promoter SEQ ID NO: 2 as reported by Turco, E. et al., *Immunogenetics* 32:117 (1990). The primers, SEQ ID NO: 3 and SEQ ID NO: 4, were selected so that the first primer, SEQ ID NO: 3, was centered on the tail of one protein binding or recognition sequence and included the head of the next adjacent one. Alternatively, between about 4 to 8 more nucleotides may be added at the oligomer junctions, to create a restriction site between the multiple recognition sequences of the polymers. As seen in FIG. 4, TATC was added at both the 3' and 5' ends of the protein binding sequence to create EcoRV restriction sites (GATATC). The 3' ends of the primers must also be carefully selected to avoid undesirable primer artifacts. In the present example the stretches of A's and T's were positioned near the centers of the primers rather than at the 3' ends, by extending the length of the primers by a few bases, e.g., CTAGA. The sizes of the synthetic oligonucleotides were thereby increased to 31 bases for SEQ ID NO: 3 and 28 bases for SEQ ID NO: 4, respectively, and were used to generate polymers with repeats that were 22 nucleotides long.

As seen in FIG. 4, the first round of amplification generates first extension products SEQ ID NO: 5 and SEQ ID NO: 6 having 44 base pairs which allow for a different, staggered annealing during later steps causing progressive increase of the polymer size (SEQ ID NO: 7 and SEQ ID NO: 8).

The amplification schematically illustrated in FIG. 4 was performed in two steps. In the first step, 40 cycles of denaturation at 90° C. for 1 minute, annealing at 44° C. for 1.5 minutes, and elongation at 72° C. for 1.5 minutes were performed with 50 mM KCl, 10 mM Tris-Cl, pH 8.3, 1.5 mM MgCl$_2$, 0.01% (w/v) gelatin, 200 µM each dNTP, 3 µM each primer, and 2.0–2.5 units Taq Polymerase (Cetus, Emeryville, Calif.), in a final volume of 100 µl. The material from 3 tubes (3×100 ul) was pooled and then separated in low melting point agarose (1.7% in TAE buffer). The predominant bands, which corresponded to 4 and 5 repeat polymers (mers) were isolated, eluted, and concentrated. These polymers were in turn used as primers and templates for a second amplification using the same conditions for an additional 25 cycles. The resulting product was concentrated and washed in a Centricon device (Amicon) and phosphorylated using T4 polynucleated kinase by methods well known in the art. The phosphorylated product was then ligated into the EcoRV site of pBluescript II (Stratagene) and cloned in XL1-Blue (Stratagene) using standard methods.

Figure 5A:
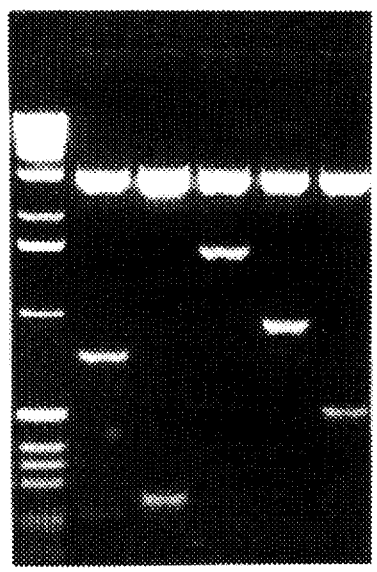
FIGS. 5A and 5B show respectively photographs of autoradiograms of polymeric cloned inserts cut from plasmid XL1-Blue by digestion with EcoRI and Hind III and of products formed by EcoRV digestion of the polymeric cloned inserts cut from plasmid XL1-Blue.
Figure 5B:
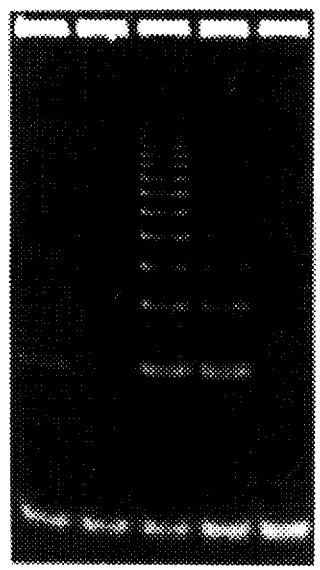

The polymeric inserts were cut from the vector by digestion with EcoRI and HindIII and separated in a 1.6% agarose gel and detected by ethidium bromide staining. FIG. 5A shows the size range of the cloned inserts which corresponds to 11–70 repeat polymers. The polymeric inserts were also digested with EcoRV and the resulting products separated in a 12% acrylamide gel. Lane 1 of FIG. 5A contains a 1 Kb reference DNA ladder. FIG. 5B shows the result of the digestion of each insert with EcoRV. In this example, the conditions for digestion were such that the larger inserts were not completely digested. The monomer units comprising 22 base pairs and multiples thereof are readily seen.

Figure 6:
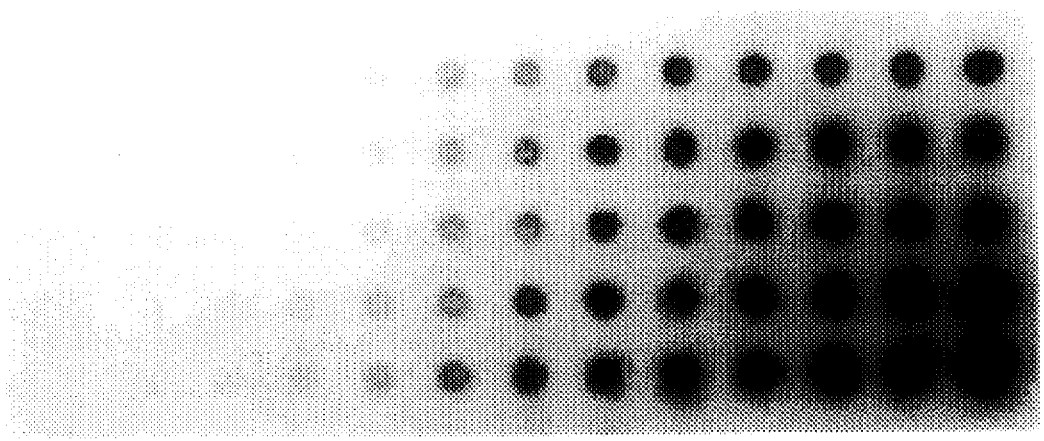
FIG. 6 is a photograph of a Nytran filter spotted with increasing quantities of DNA polymer produced by the methods of the present invention which was hybridized with a radioactively labeled probe.

The polymers were also tested for their ability to bind, once denatured, to Nytran membranes (Schleicher & Schuell, Keene, N.H.) and properly hybridize with a labeled complementary DNA sample. FIG. 6 shows increasing quantities of DNA polymer, applied on a Nytran membrane in increasing quantities from left to right in each row with a HYBRI-DOT filtration manifold (BRL). Each column contained the same quantity by mass of DNA, but the number of repeats in the polymer used in each row increases from top to bottom. The top row served as a control which was homologous to the entire test DNA sequence. The top row served as a control which was homologous to the entire probe sequence. The DNA was fixed to the membrane with a 5 minute exposure to UV light (UVP UV Transilluminator with a 302 nm filter, San Gabriel, Calif.). The filter was hybridized with a 275 base pair radioactively labeled test DNA from the HLA DQβ promotor which contained the protein binding region in FIG. 4. See, Turco, E., et al., *Immunogenetics* 32:117 (1990). As can be seen, the more efficient hybridization occurred with the longest probes.

The sizes of the monomers, polymers and annealed test DNA used in this example are similar to those that would typically be used in performing reverse dot blot procedures of the present invention.

Polymeric sequences generated according to the aforedescribed methods may also be used to prepare DNA binding protein affinity columns, and also may be used as probes which can be used for the screening of expression libraries for the search for the genes encoding proteins which bind to these specific DNA sequences.

In the following example polymers of oligonucleotides prepared in accordance with the methods of the present invention were used as the bound ligand in reverse dot blots.

EXAMPLE 2

Figure 7A:
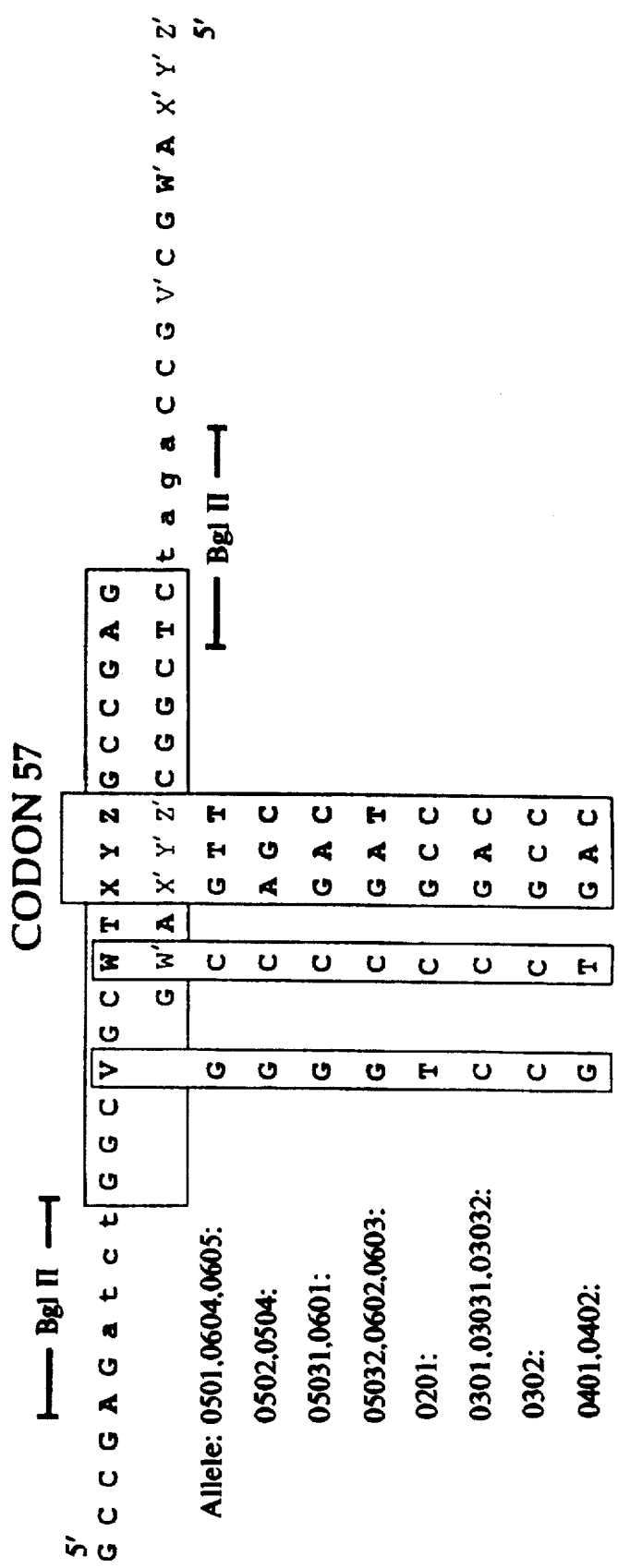
FIG. 7A shows the oligonucleotides (SEQ ID NO: 9 through SEQ ID NO: 16—top strand and SEQ ID NO: 17 through SEQ ID NO: 26—bottom strand) used to prepare DQβ allele-specific polymers encompassing codon 57. The nucleotide substitutions for SEQ ID NOS: 9–16 for V, W, X, Y, and Z in the top strand in the figure, are depicted in the three long boxes from top (SEQ ID NO: 9) to bottom (SEQ ID NO: 16). The nucleotide substitutions for SEQ ID NOS: 17–24 for W', X', Y', Z', and V' in the lower strand in the figure, are depicted in the three long boxes from top (SEQ ID NO: 17) to bottom (SEQ ID NO: 24). V', W', X', Y', and Z' represent the complementary nucleotides of V, W, X, Y, and Z, respectively.

Oligonucleotides (SEQ ID NO: 9–SEQ ID NO: 24) for the generation of polymers specific for the eight HLA-DQβ alleles centered on codon 57 of the second exon of the HLA-DQB1 gene shown in FIG. 7A (see, Morel, P., et al., *P.N.A.S.* (*USA*) 85:8111 (1988) the disclosure of which is incorporated herein by reference), were synthesized with a Millipore Cyclone Plus DNA Synthesizer (Millipore, Milford, Mass.). With reference to FIG. 7A, V, W, X, Y and Z represent the nucleotides that vary in the various DQβ alleles indicated on the left as well as the nucleotides that vary in the various primers used to generate the alleles (SEQ ID NO: 9 through SEQ ID NO: 16 for the upper primer and SEQ ID NO: 17 throught SEQ ID NO: 24 for the lower primer). The "t a g a" sequence was added to introduce a BglII site between the repeats of the allele specific sequences. V', W', X', Y' and Z' represent the complementary nucleotides of V, W, X, Y and Z, respectively.

Figure 8:
FIG. 8 is a photograph of an ethidium bromide stained agorose gel containing the polymeric cloned inserts of the eight oligonucleotide probes synthesized around codon 57 of the HLA-DQβ alleles cut from corresponding plasmids by digestion with Eco RI and HindIII and then purified.

The polymers were constructed and cloned as in Example 1. Polymeric inserts were cut from the vectors by digestion with EcoRI and HindIII, separated in a 1.6% agarose gel and purified. The purified polymers corresponding to the above DQβ alleles are seen in the agarose gel of FIG. 8. The first and last lanes contain a molecular weight marker where the uppermost band is 587 base pairs.

Figure 7B:
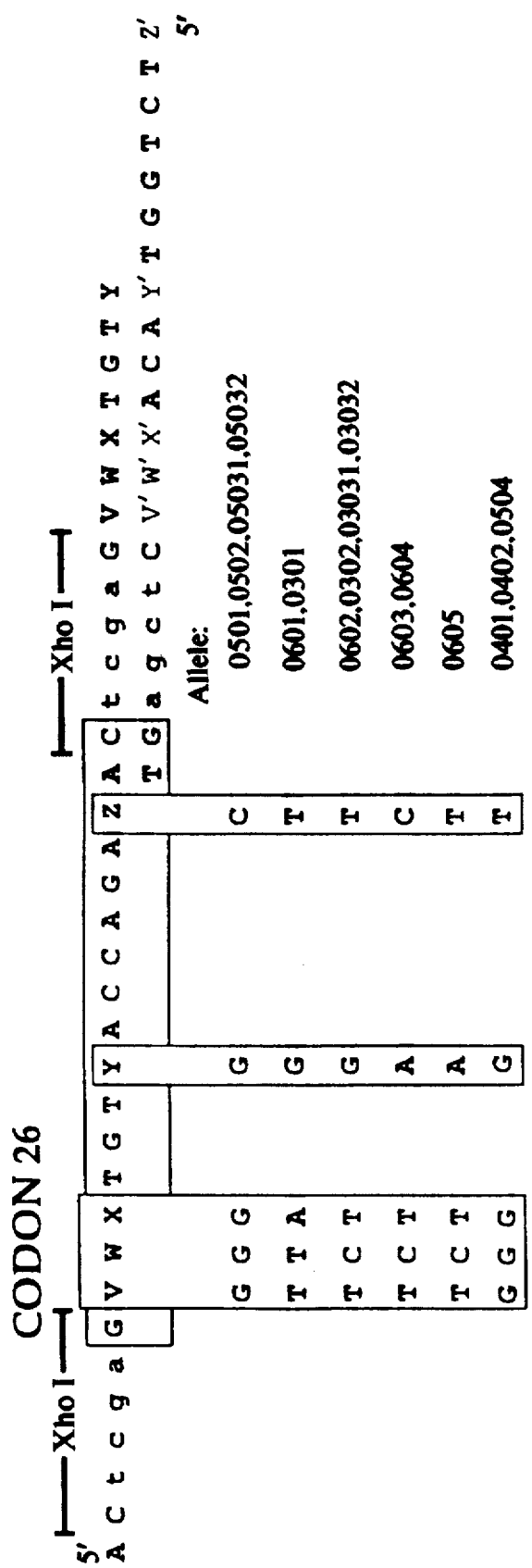
FIG. 7B shows the oligonucleotides (SEQ ID NO: 25 through SEQ ID NO: 30—top strand and SEQ ID NO: 31 through SEQ ID NO: 36—bottom strand) used to prepare DQβ allele-specific polymers encompassing condon 26. The nucleotide substitutions for SEQ ID NOS: 25–30 for V, W, X, Y, and Z in the top strand in the figure, are depicted in the three long boxes from top (SEQ ID NO: 25) to bottom (SEQ ID NO: 30). The nucleotide substitutions for SEQ ID NOS: 31–36 for W', X', Y', Z', and V' in the lower strand in the figure, are depicted in the three long boxes from top (SEQ ID NO: 31) to bottom (SEQ ID NO: 36). V', W', X', Y', and Z' represent the complementary nucleotides of V, W, X, Y, and Z, respectively.

In order to distinguish between the pairs of alleles characterized by the same oligonucleotide centered on condon 57, another 5 polymers need to be added to the filter. These additional oligonucleotides can be chosen to represent another variable segment. For example, the segment centered on condon 26 was used with the sequences shown in FIG. 7B (SEQ ID NO: 25 through SEQ ID NO: 30 for the upper primer and SEQ ID NO: 31 through SEQ ID NO: 36 for the lower primer). A few more polymers at other positions are necessary to distinguish less common variations. See, XI International HLA Workshop Reference Protocols (1990); Marsh, S. G., et al., *Human Immunol.* 31:207 (1991), the disclosures of which are incorporated herein by reference.

Figure 9A:
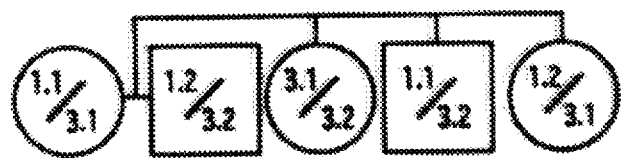
FIGS. 9A and 9B show, respectively, photographs of molecular typing results obtained using traditional dot blot, and the present method for a family which carries many alleles that vary at codon 57 of the DQβ locus.
Figure 9A:
Figure 9A:
Figure 9A:
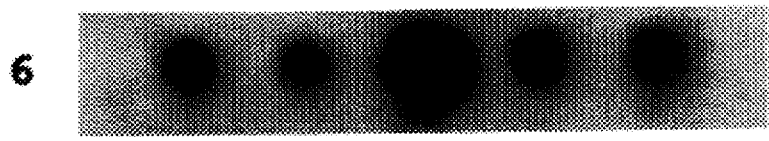
Figure 9A:

FIGS. 9A and B show the results obtained by using the traditional dot-blot method (A) and the method of the present invention (B). The members of Family 5514 of the Children's Hospital of Pittsburgh Insulin-Dependent Diabetes Mellitus (IDDM) Registry were chosen because they serve to demonstrate the sensitivity of the method of the present invention in distinguishing, for example, the alleles DQB1*0301 and DQB1*0302. See, Morel, P., et al., *P.N.A.S. USA* 85:8111 (1988) and Trucco, G., et al., *Diabetes*

Figure 9B:
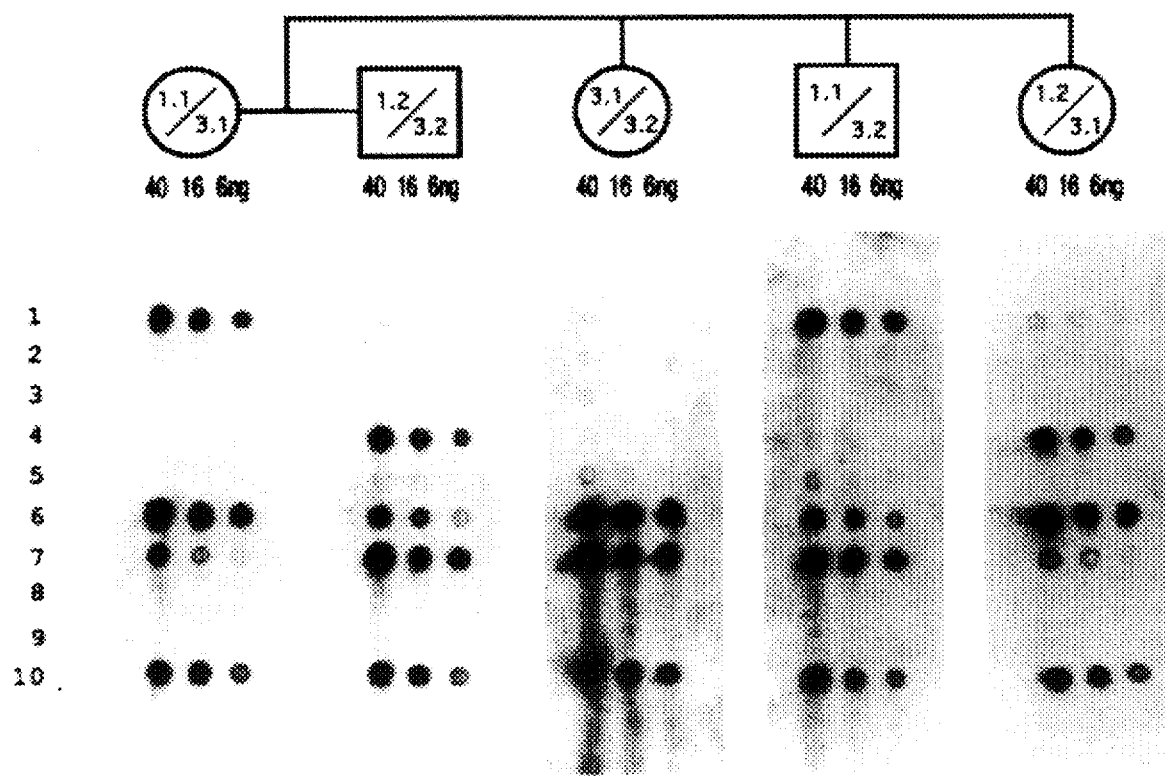

38:1617 (1989), the disclosures of which are incorporated herein by reference. These alleles, which only differ by one base change in codon 57, are considered critical markers for susceptibility to IDDM. Id. Family 5514 had previously been typed serologically, and this typing is shown in the family tree. The results shown in FIG. 9A were obtained using the conventional dot blot procedure using radioactively labeled, allele-specific oligonucleotides which correspond to the sequences in rows 1, 4, 6 and 7 in FIG. 7A. Id. In FIG. 9B, the results were obtained instead by using biotinylated primers for the amplification and the non-radioactive FLASH Detection System (Stratagene). The results in FIG. 9B were derived by using nylon filters (FLASH, Stratagene) on which were spotted titrated amounts (40, 16, 6 ng, left to right, respectively) of the various polymers previously shown in FIG. 8. Rows 1 to 8 contain the polymers of the oligonucleotides encompassing codon 57 in the order shown in FIG. 7A. Row 9 contains equivalent amounts of a linearized plasmid (pBluescript II SK-, Stratagene) as a negative control. The positive control is in row 10. This polymer contains the sequence CTTCGACAGCGACGTGG, (SEQ ID NO: 1) centered at amino acid 42, that is shared by all the DQβ1 alleles. Once dried, these filters were treated with 0.4N NaOH followed by washing with 1.5M NaCl, 0.1M NaH$_2$PO$_4$, 10 mM EDTA, pH 7.4, and then exposed to UV light to cross-link the denatured polymers to the membrane. After hybridization of the amplified test DNA, the filters were stringently washed with tetramethylammonium chloride at 57° C. as described by Wood, W. I., et al., P.N.A.S. USA 82:1585 (1985). In both experiments (A and B) the primers used for the amplification were those described by Dorman, J., et al., P.N.A.S. USA 87:7370 (1990); Morel, P., et al., P.N.A.S. USA 85:8111 (1988); and Trucco, G., et al., Diabetes 38:1617 (1989), the disclosures of which are incorporated herein by reference.

Figure 10:
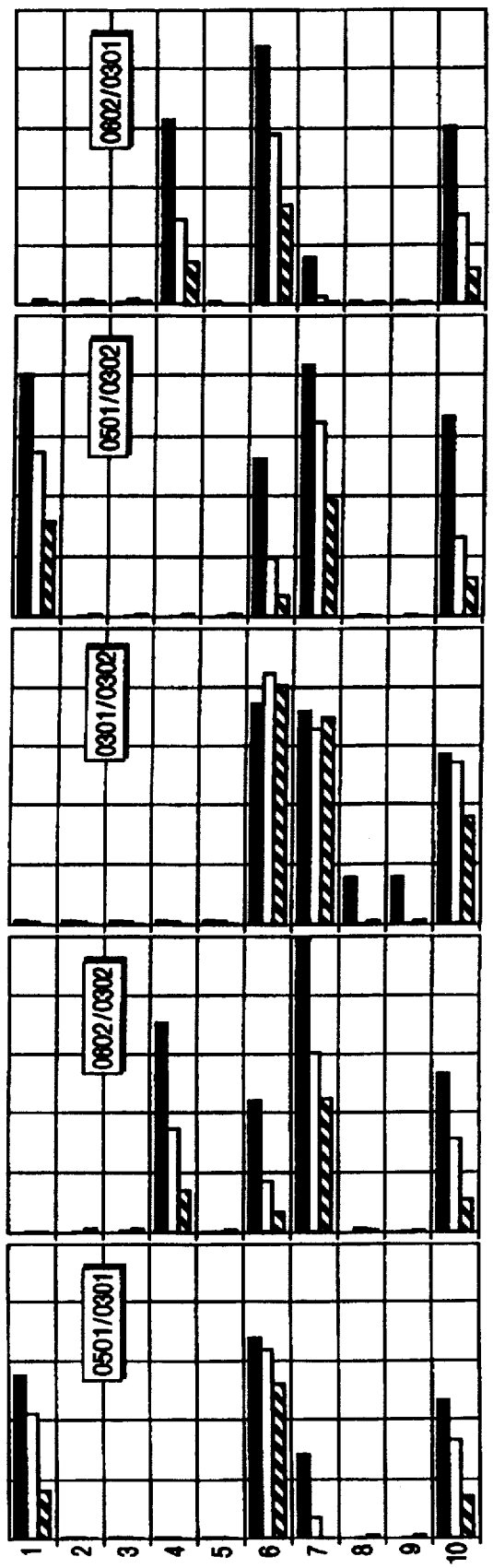
FIG. 10 shows image analysis of the corresponding reverse dot blots of FIG. 9B.

The reverse dot blot results achieved according to the present invention shown in FIG. 9B were subjected to image analysis. The dot blot results were scanned (300 ZS Scanner, Microtek) for analysis with a personal computer (Macintosh IIcx, Apple). The integrated densities of the spots at the positions of the three different spotted polymer concentrations (black (left): 40 ng, white (middle): 16 ng, hatched (right): 6 ng) were determined using the method described by Rasbond, W., Image 37, National Institutes of Health, Public Domain (1991). The results are shown in FIG. 10. The computer automatically determines the typing using an algorithm, based on the densities relative to the positive and negative controls. See, FIG. 9B. The applied amount of DNA for the positive control was empirically determined so that the signal intensity corresponded to the minimal level which would be considered positive for the other specific sequence polymers. In the illustrated examples, each of the individuals is positive for two of the oligonucleotide polymers. Although some of the cross-reaction is apparent between the allelic 0301 and 0302 sequences, these intensities are significantly lower than the positive controls. When the film is overexposed as in the case of the 0301/ 0302 individual of the family (FIG. 9B), the highest dilutions assist in rapidly obtaining the correct results. For economy and simplicity it is advantageous to spot the polymers of the specific sequences of all the alleles at all the loci (with their relative controls), on a single, relatively small filter, using a robotic arm. The same filter can be used to type alleles at any locus because the amplified material will be made specific by using labeled gene-specific oligonucleotide primers.

As shown in the foregoing example, thirteen different polymers are sufficient to properly type the recognized DQβ allelic forms. However, certain heterozygous combinations lead to ambiguities which can be resolved with five additional polymer probes. Although in most cases these probes will provide redundant information, their use will document the internal consistency of the method. DQα, DPβ, and DPα allele specific oligonucleotides can easily be generated using the same strategy. DRα does not constitute a problem since it is not polymorphic. It is added to the particular substrate being used as well, to constitute an internal positive control. In the case of DRβ allelic variants, the system becomes too complex to be easily solved as for the alleles at the other loci. At least two genes are co-expressed in each cell, e.g., DRB1 and DRB3, or DRB1 and DRB4; second, different alleles frequently contain the same variable segments but in different combinations with other variable segments. This patchwork of identical, short DNA stretches present in different allelic sequences, will make the use of only one oligonucleotide per allele insufficient, particularly if the oligonucleotides are used to type heterozygous individuals. This problem can be solved, however, by using allele specific primers for the initial enzymatic amplification of the DNA. Three allele specific amplifications are necessary to recognize all the molecular allelic forms present in the DR1, DR2, and DR4 allelic "families", primer pairs for which are respectively: SEQ ID NO: 37 and SEQ ID NO: 38; SEQ ID NO: 39 and SEQ ID NO: 40; and SEQ ID NO: 41 and SEQ ID NO: 42. In addition, the DRB1 alleles associated with the DRw52 locus form the fourth group to be amplified with a group specific primer SEQ ID NO: 43 and SEQ ID NO: 44. An additional primer must also be synthesized to distinguish the real DRw52 alleles SEQ ID NO: 45 and SEQ ID NO: 46. Based on the XI International Histocompatibility Workshop, all the specific oligonucleotides that must be transformed in repetitive polymers to test all the DRB sequences are listed in FIG. 11 with the group specific primer pairs. The oligonucleotides are: SEQ ID NO: 47 through SEQ ID NO: 59 (DRB1001–DRB1013); SEQ ID NO: 60 through SEQ ID NO: 62 (DRB8601–DRB8603); SEQ ID NO: 63 through SEQ ID NO: 71 (DRB5701–DRB5709); SEQ ID NO: 72 through SEQ ID NO: 84 (DRB2801–DRB2813); SEQ ID NO: 85 through SEQ ID NO: 96 (DRB7001–DRB7012); and SEQ ID NO: 97 through SEQ ID NO: 112 (DRB3701–DRB3716).

Five amplifications are therefore necessary to fully type DRβ, bringing to 11 the number of independent amplifications to be completed: 2 for DQα and β, 2 for DPα and β, 1 for DRβ all segments, 1 for DRα, and 5 for DRβ allele specific segments. While this number is not prohibitive, it can be substantially reduced by performing co-amplifications that will reduce the number of independent reactions necessary to generate all the segments specifically representing DR, DQ, and DP α and β chain gene hypervariable regions.

In general, it is important to determine the most appropriate conditions for the simultaneous hybridization of all the various co-amplified genomic DNA stretches while guaranteeing extremely selective binding of the appropriate allele specific polymers. In the normal reverse dot blot method care must be devoted to choose the various oligonucleotides in a way that they share, on the basis of their nucleotide composition, the same melting point. In this way the same stringency conditions can be used for all the probes, while still conserving the desired specificity of each probe. Although this would not be impossible with the foregoing experimental conditions, more freedom in selecting appropriate oligonucleotides for the present polymer preparations can be obtained by using the method of Wood, W. I., et al., *P.N.A.S.* (*USA*) 82:1585 (1985), the disclosure of which is incorporated herein by reference. By modifying the ionic conditions, the stringency of the hybridization becomes independent of G/C content and is only a function of temperature and the length of the annealing segment. For this reason, probe polymers are designed so that the annealing segment is consistently of the same size. The method requires washing of the hybridized filters once with 6×SSC, 0.1% SDS at room temperature to remove excess probe, and then twice with 3.0M tetramethylammonium chloride, 50 mM Tris-HC1 (pH 8.0), 2 mM EDTA, 0.1% SDS at room temperature to exchange sodium ions with tetramethylammonium ions. The filters are then stringently washed with the same solution at 57° C. Once prepared, each of the polymers is evaluated under these conditions to ensure that the washing is behaving as expected and if necessary, adjustments are made to the probe length or its exact position to obtain the most uniform characteristics for all of the polymer probes.

Another aspect of the present invention allows for the substitution of radioactive isotopes with less dangerous tracers for DNA labeling. A useful approach for eliminating all the problems related to the use of the radioactivity, is the one using biotin (vitamin H) to label the primers for enzymatic amplification. The modified primers are commercially available from numerous sources such as Genosys Biotechnologies, Inc. (The Woodlands, Tex.). Alternatively, biotinylated nucleotides can be used during the enzymatic amplification of the various DNA segments of interest.

Analogs of thymidine and thymidine triphosphate are known that contain a biotin molecule covalently bound to the C-5 position of the pyrimidine ring through an allylamine linker arm as described by Langer, P., et al., *P.N.A.S.* (*USA*) 78:6633 (1981), the disclosure of which is incorporated herein by reference. Polynucleotides can be generated that contain 50 molecules of biotin per kb. These probes have denaturation, reassociation and hybridization characteristics similar to those of controls that do not have biotin substitutions. Many of biotin's features make these probes more suitable for the present purposes than radioactive probes. In fact, the interaction between biotin and avidin, a 68,000 dalton glycoprotein from egg white, has one of the highest binding constants known ($K_{dis}=10^{-15}$). Therefore, biotinylated DNA stretches can be recognized simply by adding an appropriate indicator molecule coupled with avidin to the hybridized DNA. Such indicators can be fluorescent dyes, electron-dense proteins, enzymes, or antibodies. A notable feature of avidin molecules is that they can multiply the number of indicator molecules that can attach to the biotin residues, thus enhancing detection.

AS an alternative, anti-biotin antibodies can be used without avidin to detect or locate specific sequences in the DNA fixed to a matrix. For example, protocols have been developed that use either rabbit anti-biotin antibodies and fluorescein-labeled goat anti-rabbit IgG or antibodies conjugated with alkaline phosphate to turn a colorless substrate (5-bromo-4-chloro-3-indolyl phosphate or nitro blue tetrazolium salt [NTB]) into a purple blue precipitate, thus identifying the positions of the hybridized biotinylated DNAs.

Kits for non-radioactive DNA labeling and detection are also commercially available. One of them, from Boehringer Mannheim Biochemicals, uses the same technical approach: the dUTP is linked via a spacer arm to the steroid hapten digoxigenin (Dig-dUTP). Hybridized DNA is detected by enzyme-linked immunoassay using a specific anti-digoxigenin antibody conjugated with alkaline phosphate and an appropriate enzyme-catalyzed color reaction. More recently chemiluminescent detection systems have become available for detecting both biotin and digoxigenin-modified nucleotides. Another nonradioactive detection kit is the Flash Detection System (Stratagene) which detects biotinylated DNA's with a chemiluminescent process. A chemiluminescent substrate is also available for the Boehringer-Mannheim kit. Biotin or digoxigenin can also be attached to the test DNA after its synthesis by using photoreactive biotin or photodigoxigenin (Boehringer Manneheim). An additional alternative for detection involves the attachment of an enzyme of the detection system. Such an enzyme can be attached either to the oligonucleotide primers or to the test DNA after synthesis. This method may be performed with the Lightsmith I labeling system (Promega, Madison, Wis.) wherein the enzyme alkaline phosphatase is coupled to an amino modified oligonucleotide primer or incorporated deoxyribonucleotide and is later treated with a chemiluminescent substrate.

The forgoing detection approaches offer many advantages over the use of radioactivity. For example, results are available in a short period of time, and the primers are stable so that they do not have to be freshly prepared each time. In addition, any laboratory can perform these techniques because they use only non-hazardous materials.

This approach solves many of the problems presented by the use of radioactive labeling and can be used in the present method since a very high signal is generated by hybridizing polymers of the probes. All the reagents and methods herein described can be combined into an automated system so that a complete class II or other typing can be obtained by hybridizing all of the amplified products to a single filter and having the results interpreted automatically. Such automation would greatly reduce the manual manipulations involved in a complete typing and facilitate the accurate interpretation of the large amount of data generated for each typing. The labor reduction is achieved by creating in advance a filter containing all of the necessary polymers of the probes. Once the appropriate polymers and their combinations are established, the dot blotting process can easily be performed by a robotic work station and a large number of the filters can be prepared automatically. Kits for a given typing can therefore contain a substrate to which is bound all the probes required and a standardized template to interpret the results.

The interpretation of the results can be automated by using a scanning device to enter the raw data directly to a computer. In order to do this, it is important to standardize as much as possible the intensity of the positive and negative signals on the filters. To distinguish between positive and negative reactions the computer will refer to the intensity of the signals generated by both the always positive reaction against the DRα polymer and a DNA, like *E. coli* DNA, that has no similarity to the amplified human segments. In the case of the individual polymers of the probes, it will be necessary to adjust the exact amounts which are applied to the filters so when a labeled DNA is correctly hybridized the positive signal has a uniform intensity. Once the system is able to properly identify the positive and negative reactions, the positions of the various positive spots on the filters will be used to determine the corresponding specificity. The computer must be programmed in a way that is also able to correlate the presence of positive spots at two or three different positions, since sometimes it is necessary to generate an exclusive pattern, specific for those alleles that cannot be recognized among the others by a single oligonucleotide polymer. DR β alleles are paradigmatic of these situations. Based on sufficient internal controls a simple algorithm can be designed that automatically converts positive spot positions into a complete conventional HLA class II typing.

The foregoing methods and examples are not in any way limited to HLA class II typing. The methods of the present invention are equally applicable to the detection of aberrant gene sequences which have been found, for example, in cystic fibrosis, Marfan's syndrome, muscular dystrophies, hemaglobinopathies, 21-hydroxylase deficiency or any other case where the particular sequence variations become known.

Although the invention has been described in detail for the purposes of illustration, it is to be understood that such detail is solely for that purpose and that variations can be made therein by those skilled in the art without departing from the spirit and scope of the invention except as it may be limited by the claims.

We claim:

1. A method of detecting the presence of nucleic acid sequences, comprising:
  binding polymers of at least one oligonucleotide probe to a substrate wherein said polymeric probes are comprised of monomeric sequence units that are complementary to a target sequence which exists as a single copy within a region of a nucleotide sequence contained in a DNA test sample wherein said monomeric sequence units are selceted from the group consisting of Sequence I.D. Nos. 1–112;
  contacting said substrate to which said polymeric probes are bound with amplification products of said test DNA sample containing uncharacterized oligonucleotide sequences, wherein a reporter moiety has been incorporated, such that individual complementary sequences that are contained in the amplified test sample are able to anneal to any monomeric sequence that is contained in any polymeric probe bound to said substrate;
  washing said substrate to remove unannealed amplified DNA test sample from said substrate; and
  detecting the presence or absence of reporter moieties retained by said polymeric probes on said substrate.

2. The method of claim 1, wherein said substrate is a nylon membrane.

3. The method of claim 1, wherein said substrate is a nitrocellulose membrane.

4. A method of synthesizing oligonucleotides probes consisting of repeated monomeric sequence units by the steps of:

(a) annealing two oligonucleotide primers which are oppositely oriented and which are complementary at their 3' ends and which together either directly or in the form of complementary nucleotides define the sequence of a complete monomeric unit which incorporates the selected oligonucleotide probe sequence as well as a sufficient number of the nucleotides of the adjacent monomeric units such that the primers anneal at their 3' ends and that the 5' ends of the primers are not annealed and function as templates for synthesis of first extension products;

(b) treating the primers with a DNA polymerase in the presence of deoxyribonucleotides such that a first extension product of each primer is synthesized which is complementary to each template;

(c) separating the complementary first extension products by denaturation to produce single-stranded molecules;

(d) annealing complementary strands of said first extension products at their 3' ends in a staggered arrangement such that the 5' ends are not annealed and function as templates for further extension of the previous extension products;

(e) treating the annealed strands using a DNA polymerase and deoxyribonucleotides such that double-stranded extension products are synthesized;

(f) separating the complementary extension products by denaturization; and (g) repeating steps (d) through (f) using the extension products of step (f) to produce successively longer extension products with each repetition without the addition of any new primer sequences not generated by the initial two oligonucleotide primers.

5. The method of claim 4, further comprising after step (c) the steps of:

(c') treating the single-stranded first extension products generated in step (c) with the primers of step (a) under conditions such that additional molecules of the first extension products are synthesized using single strands of the first extension products as templates; and (c") optionally repeating steps (c) and (c') to further increase the quantity of the first extension products.

6. The method of claim 4, wherein said denaturing is caused by heating.

7. The method of claim 4, wherein longer starting oligonucleotide primers are used which are substantially equivalent to said first extension products such that steps (a)–(c) are deleted.

8. The method of claim 5, wherein the products of each step are not purified such that the step (g) repetition occurs simultaneously with the repetitions of steps (c) and (c') when there is a sufficient concentration of first extension products that step (d) annealing occurs.

9. The method of claim 4, wherein said DNA polymerase is selected from the group consisting of E.coli DNA polymerase I, Klenow fragment of E.coli DNA polymerase I, T4 DNA polymerase, and T7 DNA polymerase.

10. The method of claim 4, wherein said DNA polymerase is a thermostable DNA polymerase selected from the group consisting of *Thermus aqaticus* DNA polymerase, *Thermococcus litoralis* DNA polymerase, and *Pyrococcus furiosus* DNA polymerase, and the repetitive cycles of step (g) are achieved by cycling the reaction temperature successively from temperatures suitable for annealing, extension, and denaturing.

11. The method of claim 4 further comprising the step of:

cloning the final double-stranded primer extension product in a vector.

12. The method of claim 11, wherein said cloned primer extension product is repetitiously duplicated within said vector by directional cloning to further increase the quantity of probe sequence inserted in the vector.

13. The method of claim 11 wherein said vector has been derived from pUC18, pUC19, or the bacteriophage M13mp series.

14. The method of claim 1, wherein entire vectors containing said polymeric probes are bound to said substrate.

15. The method of claim 1, where said polymers are single-stranded DNAs.

16. The method of claim 1 wherein said reporter moiety is selected from among $^{32}$p, biotin, and digoxigenin, wherein said reporter moiety is attached to one or both of said primers prior to synthesis of said amplification products.

17. The method of claim 1, wherein said amplification products are modified by attaching a reporter moiety after said products are synthesized.

18. The method of claim 1, wherein said reporter moiety is an enzyme which is covalently attached to the test DNA and wherein said enzyme functions as part of the detection system.

19. A substrate to which selected long polymers of at least one oligonucleotide probe are bound wherein said polymeric probes are comprised of monomeric sequence units that are complementary to a target sequence which exists as a single copy within a region of a nucleotide sequence contained in a DNA test sample wherein said monomeric sequence units are selected from the group consisting of Sequence I.D. Nos. 1–112.

20. The substrate of claim 19 wherein said monomeric sequence unit of each said polymeric probes contains about 12 to 20 nucleotides and each polymer contains about 200–2000 base pairs.

21. The substrate of claim 20 wherein said polymeric probes are comprised of specific oligonucleotides selected from the group consisting of Class II HLA DQα, HLA DQβ, HLA DRα, HLA DRβ, HLA DPα, and HLA DPβ alleles.

22. A method of detecting the presence of nucleic acid sequences, comprising:

contacting the substrate of claim 21 with an amplified test DNA sample containing unknown oligonucleotide sequences, wherein a reporter moiety has been incorporated, such that complementary nucleotide sequences anneal;

washing said substrate to remove unannealed amplified test DNA from said substrate; and detecting the presence or absence of reporter moieties retained by said polymeric probes on said substrate.

23. The method of claim 22 further comprising the step: analyzing and interpreting the results of said detection.

* * * * *